United States Patent [19]

Heistracher et al.

[11] Patent Number: 5,888,940
[45] Date of Patent: Mar. 30, 1999

[54] SUBSTITUTED BENZOTHIAZOLS WITH HERBICIDAL ACTION

[75] Inventors: Elisabeth Heistracher, Mannheim; Gerhard Hamprecht, Weinheim; Olaf Menke, Altleiningen; Peter Schäfer, Ottersheim; Cyrill Zagar, Ludwigshafen; Karl-Otto Westphalen, Speyer; Ulf Misslitz, Neustadt; Helmut Walter, Obrigheim, all of Germany

[73] Assignee: BASF Aktiengesellschaft, Ludwigshafen, Germany

[21] Appl. No.: 11,711
[22] PCT Filed: Aug. 26, 1996
[86] PCT No.: PCT/EP96/03760
    § 371 Date: Feb. 17, 1998
    § 102(e) Date: Feb. 17, 1998
[87] PCT Pub. No.: WO97/08171
    PCT Pub. Date: Mar. 6, 1997

[30] Foreign Application Priority Data

Aug. 31, 1995 [DE] Germany .................. 195 32 048.4

[51] Int. Cl.⁶ .......................... C07D 417/04; A01N 43/78
[52] U.S. Cl. .......................... 504/243; 544/309; 544/314; 544/298
[58] Field of Search ............................. 504/243; 544/309, 544/314

[56] References Cited

FOREIGN PATENT DOCUMENTS

| 420 194 | 4/1991 | European Pat. Off. . |
| 42 41 658 | 12/1992 | Germany . |
| 92/20675 | 11/1992 | WIPO . |
| 96/06089 | 2/1996 | WIPO . |
| 97/08170 | 3/1997 | WIPO . |

*Primary Examiner*—José G. Dees
*Assistant Examiner*—Sabiha N. Qazi
*Attorney, Agent, or Firm*—Keil & Weinkauf

[57] ABSTRACT

Substituted benzothiazoles I and their salts

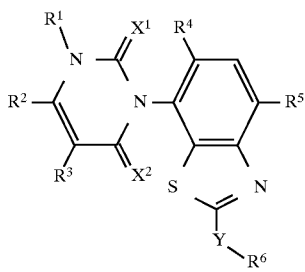

used as herbicides and for the desiccation/abscission of plants.

8 Claims, No Drawings

SUBSTITUTED BENZOTHIAZOLS WITH HERBICIDAL ACTION

This application has been filed under 35 USC 371 as a national stage application of PCT/EP96/03760 filed Aug. 26, 1996.

The present invention relates to novel substituted benzothiazoles of the general formula I $$\text{I}$$

where $X^1$ and $X^2$, independently of one another, are each oxygen or sulfur;

$R^1$ is hydrogen, amino, $C_1$–$C_6$-alkyl or $C_1$–$C_6$-haloalkyl;

$R^2$ is hydrogen, halogen, $C_1$–$C_6$-alkyl, $C_1$–$C_6$-haloalkyl, $C_1$–$C_6$-alkylthio, $C_1$–$C_6$-alkylsulfinyl or $C_1$–$C_6$-alkylsulfonyl;

$R^3$ is hydrogen, halogen or $C_1$–$C_6$-alkyl;

$R^4$ is hydrogen or halogen;

$R^5$ is cyano, halogen, $C_1$–$C_6$-alkyl, $C_1$–$C_6$-haloalkyl, $C_1$–$C_6$-alkoxy or $C_1$–$C_6$-haloalkoxy;

Y is a chemical bond, oxygen, sulfur, —SO— or —SO$_2$—;

$R^6$ is hydrogen, cyano, halogen, $C_3$–$C_6$-cycloalkyl, $C_1$–$C_6$-haloalkyl, $C_3$–$C_6$-alkenyl, $C_3$–$C_6$-haloalkenyl, $C_3$–$C_6$-alkynyl or $C_1$–$C_6$-alkyl, it being possible for the stated cycloalkyl, alkyl, alkenyl and alkynyl radicals to be substituted by cyano, $C_1$–$C_6$-alkoxy, $C_1$–$C_6$-alkylthio, ($C_1$–$C_6$-alkoxy)carbonyl, $C_1$–$C_6$-alkylaminocarbonyl, di($C_1$–$C_6$-alkyl)aminocarbonyl, ($C_1$–$C_6$-alkyl)carbonyloxy, halo-$C_1$–$C_6$-alkoxy, halo-$C_1$–$C_6$-alkylthio or $C_3$–$C_6$-cycloalkyl, with the proviso that $R^6$ may be cyano only when Y is a chemical bond, oxygen or sulfur and $R^6$ may be halogen only when Y is a chemical bond, and the agriculturally useful salts of I.

The present invention furthermore relates to the use of the compounds I as herbicides or for desiccating and/or defoliating plants, herbicides and plant desiccants/defoliants which contain the compounds I as active ingredients, processes for the preparation of the compounds I and of herbicides and plant desiccants/defoliants using the compounds I, methods for controlling undesirable plant growth and for desiccating and/or defoliating plants with the compounds I and novel intermediates of the formulae IV, V, XI and XIV, from which the compounds I are obtainable.

Herbicidal benzothiazoles having certain heterocycles in the 7 position have been disclosed in WO 92/20675 and DE-A 42 41 658. WO 92/20675 also indicates a possible desiccant/defoliant action of the compounds described there.

However, the herbicidal action of the known compounds with regard to weeds is not always completely satisfactory.

It is an object of the present invention to provide novel benzothiazoles having improved herbicidal properties. It is furthermore an object of the present invention to provide novel compounds having a desiccant/defoliant action.

We have found that these objects are achieved by the substituted benzothiazoles of the formula I which are defined at the outset. We have also found herbicides which contain the compounds I and have a very good herbicidal action. We have furthermore found processes for the preparation of these agents and methods for controlling undesirable plant growth with the compounds I.

Moreover, we have found that the compounds I are also suitable for desiccating and defoliating plant parts in crops such as cotton, potato, rape, sunflower, soybean or field beans, in particular cotton. In this context, we have found plant desiccants and/or defoliants, processes for the preparation of these agents and methods for desiccating and/or defoliating plants with the compounds I.

Depending on the substitution pattern, the compounds of the formula I may contain one or more centers of chirality and may therefore be present as enantiomer or diastereomer mixtures. The present invention relates both to the pure enantiomers or diastereomers and to the mixtures thereof.

The substituted benzothiazoles I may be present in the form of their agriculturally useful salts, the type of salt being as a rule unimportant. In general, suitable salts are the salts of those bases and those acid addition salts in which the herbicidal action is not adversely affected in comparison with the free compound I.

Particularly suitable basic salts are those of the alkali metals, preferably the sodium and potassium salts, those of the alkaline earth metals, preferably calcium and magnesium salts, those of the transition metals, preferably zinc and iron salts, and ammonium salts in which the ammonium ion may, if desired, carry from one to four $C_1$–$C_4$-alkyl or hydroxy-$C_1$–$C_4$-alkyl substituents and/or a phenyl or benzyl substituent, preferably diisopropylammonium, tetramethylammonium, tetrabutylammonium, trimethylbenzylammonium and trimethyl-(2-hydroxyethyl)ammonium salts, and phosphonium salts, sulfonium salts, preferably tri($C_1$–$C_4$-alkyl)sulfonium salts, and sulfoxonium salts, preferably tri($C_1$–$C_4$-alkyl)sulfoxonium salts.

Examples of the acid addition salts are primarily the hydrochlorides and hydrobromides, sulfates, nitrates, phosphates, oxalates and dodecylbenzenesulfonates.

The organic moieties stated in the definition of the substituents $R^1$ to $R^6$ are—as in the case of halogen—general terms for individual lists of the individual group members. All carbon chains, ie. all alkyl, haloalkyl, alkoxy, alkylthio, alkylsulfinyl, alkylsulfonyl, haloalkoxy, haloalkylthio, alkoxycarbonyl, alkylaminocarbonyl, dialkylaminocarbonyl, alkylcarbonyloxy, alkenyl, haloalkenyl and alkynyl moieties, may be straight-chain or branched. Polyhalogenated haloalkyl, haloalkoxy, haloalkylthio and haloalkenyl radicals may carry identical or different halogen atoms.

The specific meanings are, for example, as follows:

halogen: fluorine, chlorine, bromine or iodine;

$C_1$–$C_6$-alkyl and the alkyl moieties of ($C_1$–$C_6$-alkyl)carbonyloxy, $C_1$–$C_6$-alkylaminocarbonyl, di($C_1$–$C_6$-alkyl)aminocarbonyl, ($C_1$–$C_6$-alkyl)carbonyloxy-$C_1$–$C_6$-alkyl, $C_1$–$C_6$-alkylaminocarbonyl-$C_1$–$C_6$-alkyl, di($C_1$–$C_6$-alkyl)aminocarbonyl-$C_1$–$C_6$-alkyl, $C_1$–$C_6$-alkylaminocarbonyl-$C_3$–$C_6$-alkenyl, di($C_1$–$C_6$-alkyl)aminocarbonyl-$C_3$–$C_6$-alkenyl, $C_1$–$C_6$-allylaminocarbonyl-$C_3$–$C_6$-alkynyl, di($C_1$–$C_6$-alkyl)aminocarbonyl-$C_3$–$C_6$-alkynyl, $C_1$–$C_6$- alkylaminocarbonyl-$C_3$–$C_6$-cycloalkyl and di($C_1$–$C_6$-alkyl)aminocarbonyl-$C_3$–$C_6$-cycloalkyl: methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

cyano-$C_1$–$C_6$-alkyl: for example cyanomethyl, 1-cyanoethyl, 2-cyanoethyl, 1-cyanoprop-1-yl, 2-cyanoprop-1-yl, 3-cyanoprop-1-yl, 1-cyanobut-1-yl, 2-cyanobut-1-yl, 3-cyanobut-1-yl, 4-cyanobut-1-yl, 1-cyanobut-2-yl, 2-cyanobut-2-yl, 3-cyanobut-2-yl, 4-cyanobut-2-yl, 1-(cyanomethyl)-eth-1-yl, 1-(cyanomethyl)-1-(methyl)-eth-1-yl, 1-(cyanomethyl) prop-1-yl and 2-cyanohex-6-yl;

$C_1$–$C_6$-haloalkyl: $C_1$–$C_6$-alkyl as stated above, which is partially or completely substituted by fluorine, chlorine, bromine and/or iodine, eg. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, petafluoroethyl [sic], 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptaluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_1$–$C_6$-alkoxy and the alkoxy moieties of $C_1$–$C_6$-alkoxy-$C_1$–$C_6$-alkyl, $C_1$–$C_6$-alkoxy-$C_3$–$C_6$-alkenyl, $C_1$–$C_6$-alkoxy-$C_3$–$C_6$-alkynyl, $C_1$–$C_6$-alkoxy-$C_3$–$C_6$-cycloalkyl, ($C_1$–$C_6$-alkoxy)carbonyl, ($C_1$–$C_6$-alkoxy)carbonyl-$C_1$–$C_6$-alkyl, ($C_1$–$C_6$-alkoxy)carbonyl-$C_3$–$C_6$-alkenyl, ($C_1$–$C_6$-alkoxy)carbonyl-$C_3$–$C_6$-alkynyl [sic] and ($C_1$–$C_6$-alkoxy)carbonyl-$C_3$–$C_6$-cycloalkyl: methoxy, ethoxy, n-propoxy, 1-methylethoxy, n-butoxy, 1-methylpropoxy, 2-methylpropoxy, 1,1-dimethylethoxy, n-pentyloxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexyloxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$–$C_6$-haloalkoxy and the haloalkoxy moieties of $C_1$–$C_6$-haloalkoxy-$C_1$–$C_6$-alkyl, $C_1$–$C_6$-haloalkoxy-$C_3$–$C_6$-alkenyl, $C_1$–$C_6$-haloalkoxy-$C_3$–$C_6$-alkynyl and $C_1$–$C_6$-haloalkoxy-$C_3$–$C_6$-Cycloalkyl: $C_1$–$C_6$-alkoxy as stated above, which is partially or completely substituted by fluorine, chlorine, bromine and/or iodine, eg. chloromethoxy, dichloromethoxy, trichloromethyloxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, petafluoroethoxy [sic], 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy, 5-fluoropentyloxy, 5-chloropentyloxy, 5-bromopentyloxy, 5-iodopentyloxy, undecafluoropentyloxy, 6-fluorohexyloxy, 6-chlorohexyloxy, 6-bromohexyloxy, 6-iodohexyloxy and dodecafluorohexyloxy;

$C_1$–$C_6$-alkylthio and the alkylthio moieties Of $C_1$–$C_6$-alkylthio-$C_1$–$C_6$-alkyl, $C_1$–$C_6$-alkylthio-$C_3$–$C_6$-alkenyl, $C_1$–$C_6$-alkylthio-$C_3$–$C_6$-alkynyl and $C_1$–$C_6$-alkylthio-$C_3$–$C_6$-cycloalkyl: methylthio, ethylthio, n-propylthio, 1-methylethylthio, n-butylthio, 1-methylpropylthio, 2-methylpropylthio, 1,1-dimethylethylthio, n-pentylthio, 1-methylbutylthio, 2-methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethyl butylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio, preferably methylthio and ethylthio;

$C_1$–$C_6$-haloalkylthio and the haloalkylthio moieties of $C_1$–$C_6$-haloalkylthio-$C_1$–$C_6$-alkyl, $C_1$–$C_6$-haloalkylthio-$C_3$–$C_6$-alkenyl, $C_1$–$C_6$-haloalkylthio-$C_3$–$C_6$-alkynyl and $C_1$–$C_6$-haloalkylthio-$C_3$–$C_6$-cycloalkyl: $C_1$–$C_6$-alkylthio as stated above, which is partially or completely substituted by fluorine, chlorine and/or bromine, eg. difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2, 2-trifluoroethylthio, 2,2, 2-trichloroethylthio, 2-chloro-2-fluoroethylthio, 2-chloro-2, 2-difluoroethylthio, 2, 2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3, 3-trifluoropropylthio, 3,3, 3-trichloropropylthio, 2,2,3,3, 3-pentafluoropropylthio, heptafluoropropylthio, 1-(fluoromethyl )-2-fluoroethylthio, 1-(chloromethyl )-2-chloroethylthio, 1-(bromomethyl)-2-bromoethylthio, 4-fluorobutylthio, 4-chlorobutylthio, 4-bromobutylthio, 5-fluoropentylthio, 5-chloropentylthio, 5-bromopentylthio, 5-iodopentylthio, andecafluoropentylthio, 6-fluorohexylthio and 6-chlorohexylthio;

$C_1$–$C_6$-alkylsulfinyl, such as methylsulfinyl, ethylsulfinyl, n-propylsulfinyl, 1-methylethylsulfinyl, n-butylsulfinyl, 1-methylpropylsulfinyl, 2-methylpropylsulfinyl, 1,1-dimethylethylsulfinyl, n-pentylsulfinyl, 1-methylbutylsulfinyl, 2-methylbutylsulfinyl, 3-methylbutylsulfinyl, 1,1-dimethylipropylsulfinyl, 1,2-dimethylpropylsulfinyl, 2,2-dimethylpropylsulfinyl, 1-ethylpropylsulfinyl, n-hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$–$C_6$-alkylsulfonyl: methylsulfonyl, ethylsulfonyl, n-propylsulfonyl, 1-methylethylsulfonyl, n-butylsulfonyl, 1-methylpropylsulfonyl, 2-methylpropylsulfonyl, 1,1-dimethylethylsulfonyl, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_3$–$C_6$-cycloalkyl and the cycloalkyl moieties of $C_3$–$C_6$-cycloalkyl-$C_3$–$C_6$-alkenyl, $C_1$–$C_6$-cycloalkyl-$C_3$–$C_6$-alkynyl and $C_3$–$C_6$-Cycloalkyl-$C_3$–$C_6$-cycloalkyl: cyclopropyl, cyclobutyl, cyclopentyl and cyclohexyl;

$C_3$–$C_6$-cycloalkyl-$C_1$–$C_6$-alkyl: for example cyclopropylmethyl, cyclobutylmethyl, cyclopentylmethyl, cyclohexylmethyl, 2-(cyclopropyl)ethyl, 2-(cyclobutyl)ethyl, 2-(cyclopentyl)ethyl, 2-(cyclohexyl)ethyl, 3-(cyclopropyl)propyl, 3-(cyclobutyl)propyl, 3-(cyclopentyl)propyl, 3-(cyclohexyl)propyl, 4-(cyclopropyl)butyl, 4-(cyclobutyl)butyl, 4-(cyclopentyl)butyl, 4-(cyclohexyl)butyl, 5-(cyclopropyl)pentyl, 5-(cyclobutyl)pentyl, 5-(cyclopentyl)pentyl, 5-(cyclohexyl)pentyl, 6-(cyclopropyl)hexyl, 6-(cyclobutyl)hexyl, 6-(cyclopentyl)hexyl and 6-(cyclohexyl)hexyl;

$C_3$–$C_6$-alkenyl and the alkenyl moieties of $C_1$–$C_6$-alkoxy-$C_3$–$C_6$-alkenyl, $C_1$–$C_6$-alkylthio-$C_3$–$C_6$-alkenyl, ($C_1$–$C_6$-alkoxy)carbonyl-$C_3$–$C_6$-alkenyl, $C_1$–$C_6$-alkylaminocarbonyl-$C_3$–$C_6$-alkenyl, di($C_1$–$C_6$-alkyl)aminocarbonyl-$C_3$–$C_6$-alkenyl, ($C_1$–$C_6$-alkyl)carbonyloxy-$C_3$–$C_6$-alkenyl, $C_1$–$C_6$-haloalkoxy-$C_3$–$C_6$-alkenyl, $C_1$–$C_6$-haloalkylthio-$C_3$–$C_6$-alkenyl and $C_3$–$C_6$-cycloalkyl-$C_3$–$C_6$-alkenyl: prop-1-en-1-yl, prop-2-en-1-yl, 1-methyl-ethenyl, n-buten-1-yl, n-buten-2-yl, n-buten-3-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methyl-but-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethyl-but-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl;

cyano-$C_3$–$C_6$-alkenyl: for example 2-cyanoallyl, 3-cyanoallyl, 4-cyanobut-2-enyl, 4-cyanobut-3-enyl and 5-cyanopent-4-enyl;

$C_3$–$C_6$-haloalkenyl: $C_3$–$C_6$-alkenyl as stated above, which is partially or completely substituted by fluorine, chlorine, bromine and/or iodine, eg. 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl and 2,3-dibromobut-2-enyl;

$C_3$–$C_6$-alkynyl and the alkynyl moieties of $C_1$–$C_6$-alkoxy-$C_3$–$C_6$-alkynyl, $C_1$–$C_6$-alkylthio-$C_3$–$c6$-alkynyl, ($C_1$–$C_6$-alkoxy)carbonyl-$C_3$–$C_6$-alkynyl, $C_1$–$C_6$-alkylaminocarbonyl-$C_3$–$C_6$-alkynyl, di($C_1$–$C_6$-alkyl)aminocarbonyl-$C_3$–$C_6$-alkynyl, ($C_1$–$C_6$-alkyl)carbonyloxy-$C_3$–$C_6$-alkynyl, $C_1$–$C_6$-haloalkoxy-$C_3$–$C_6$-alkynyl, $C_1$–$C_6$-haloalkylthio-$C_3$–$C_6$-alkynyl and $C_3$–$C_6$-cycloalkyl-$C_3$–$C_6$-alkynyl: prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex -2-yn-5-yl , n-hex -2-yn -6-yl , n-hex -3-yn -1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl;

cyano-$C_3$–$C_6$-alkynyl: for example 3-cyanopropargyl, 4-cyanobut-2-yn-1-yl, 5-cyanopent-3-yn-1-yl and 6-cyanohex-4-yn-1-yl.

In view of the use of the novel compounds of the formula I as herbicides or as compounds having a desiccant/defoliant action, the variables preferably have the following meanings, alone or in combination:

$X^1$ is oxygen;

$X^2$ is oxygen or sulfur, in particular oxygen;

$R^1$ is amino, $C_1$–$C_6$-alkyl or $C_1$–$C_6$-haloalkyl, in particular amino or $C_1$–$C_6$-alkyl, particularly preferably methyl;

$R^2$ is halogen, $C_1$–$C_6$-alkyl, $C_1$–$C_6$-haloalkyl or $C_1$–$C_6$-alkylsulfonyl, in particular $C_1$–$C_6$-haloalkyl, particularly preferably trifluoromethyl, chlorodifluoromethyl or pentafluoroethyl, very particularly preferably trifluoromethyl;

$R^3$ is hydrogen or halogen, in particular hydrogen;

$R^4$ is hydrogen, fluorine or chlorine;

$R^5$ is cyano or halogen, in particular cyano, chlorine or bromine, particularly preferably chlorine;

Y is a chemical bond, sulfur, —SO— or —SO$_2$—, in particular a chemical bond or sulfur;

$R^6$ is hydrogen, halogen, $C_3$–$C_6$-cycloalkyl, $C_1$–$C_6$-haloalkyl, $C_3$–$C_6$-alkenyl or $C_1$–$C_6$-alkyl, it being possible for the stated cycloalkyl, alkyl and alkenyl radicals to be substituted by cyano, $C_1$–$C_6$-alkoxy, ($C_1$–$C_6$-alkoxy)carbonyl, ($C_1$–$C_6$-alkyl)carbonyloxy or $C_1$–$C_6$-haloalkoxy, with the proviso that $R^6$ may be halogen only when Y is a chemical bond.

Particularly preferred compounds of the formula I are those in which $R^6$ is one of the radicals 6.5–6.63 or, when Y is a chemical bond, also one of the radicals 6.1–6.04 (Table 1):

TABLE 1

| No. | $R^6$ |
|---|---|
| 6.1 | F |
| 6.2 | Cl |
| 6.3 | Br |
| 6.4 | I |
| 6.5 | H |
| 6.6 | CH$_2$Cl |
| 6.7 | CH$_2$F |
| 6.8 | CHF$_2$ |
| 6.9 | CF$_3$ |
| 6.10 | CClF$_2$ |
| 6.11 | CCl$_2$F |
| 6.12 | CH$_2$CH$_2$CN |
| 6.13 | CH$_2$CH$_2$F |
| 6.14 | CH$_2$CH$_2$Cl |
| 6.15 | CH$_2$CH$_2$Br |
| 6.16 | CH$_2$CH$_2$I |
| 6.17 | CH$_2$CF$_3$ |
| 6.18 | CF$_2$CF$_3$ |
| 6.19 | CH$_2$CH=CH$_2$ |
| 6.20 | CH(CH$_3$)CH=CH$_2$ |
| 6.21 | CH$_2$CH=CH—CH$_3$ |
| 6.22 | CH(CH$_3$)CH=CH—CH$_3$ |
| 6.23 | CH$_2$—C≡CH |
| 6.24 | CH(CH$_3$)C≡CH |
| 6.25 | CH$_3$ |
| 6.26 | CH$_2$CH$_3$ |
| 6.27 | n-C$_3$H$_7$ |
| 6.28 | i-C$_3$H$_7$ |
| 6.29 | n-C$_4$H$_9$ |
| 6.30 | i-C$_4$H$_9$ |
| 6.31 | s-C$_4$H$_9$ |
| 6.32 | t-C$_4$H$_9$ |
| 6.33 | n-C$_5$H$_{11}$ |
| 6.34 | n-C$_6$H$_{13}$ |
| 6.35 | CH$_2$CN |
| 6.36 | CH(CH$_3$)CN |

TABLE 1-continued

| No. | $R^6$ |
|---|---|
| 6.37 | CH$_2$CH(CH$_3$)CN |
| 6.38 | CH(CH$_3$)CH$_2$CN |
| 6.39 | CH$_2$CH$_2$OCH$_3$ |
| 6.40 | CH$_2$CH$_2$OCH$_2$CH$_3$ |
| 6.41 | CH(CH$_3$)CH$_2$OCH$_3$ |
| 6.42 | CH(CH$_3$)CH$_2$OCH$_2$CH$_3$ |
| 6.43 | CH$_2$COOCH$_3$ |
| 6.44 | CH$_2$COOCH$_2$CH$_3$ |
| 6.45 | CH$_2$COOCH(CH$_3$)$_2$ |
| 6.46 | CH(CH$_3$)COOCH$_3$ |
| 6.47 | CH(CH$_3$)COOCH$_2$CH$_3$ |
| 6.48 | CH(CH$_3$)COOCH(CH$_3$)$_2$ |
| 6.49 | CH$_2$CH$_2$COOCH$_3$ |
| 6.50 | CH$_2$CH$_2$COOCH$_2$CH$_3$ |
| 6.51 | CH(CH$_2$CH$_3$)COOCH$_3$ |
| 6.52 | CH(CH$_2$CH$_3$)COOCH$_2$CH$_3$ |
| 6.53 | CH(CH(CH$_3$)$_2$)COOCH$_3$ |
| 6.54 | CH(CH(CH$_3$)$_2$)COOCH$_2$CH$_3$ |
| 6.55 | CH$_2$CH$_2$OCOCH$_3$ |
| 6.56 | CH$_2$CH$_2$OCOCH$_2$CH$_3$ |
| 6.57 | CH(CH$_3$)CH$_2$OCOCH$_3$ |
| 6.58 | CH$_2$CH(CH$_3$)OCOCH$_3$ |
| 6.59 | CH$_2$CH$_2$OCHF$_2$ |
| 6.60 | CH$_2$CH$_2$OCH$_2$CF$_3$ |
| 6.61 | cyclohexyl |
| 6.62 | CH=CH—COOCH$_3$ |
| 6.63 | CH=CH—COOCH$_2$CH$_3$ |

With regard to the use of the substituted benzothiazoles of the formula I as herbicides, the benzothiazoles Ia ($\hat{=}$ I where $R^1$=CH$_3$, $R^2$=CF$_3$, $R^3$=H, $R^5$=Cl, $X^1$ and $X^2$=O and Y=a chemical bond), in particular the compounds Ia.1 to Ia.186 of Table 2, are very particularly preferred:

TABLE 2

| No. | $R^4$ | $R^6$ |
|---|---|---|
| Ia.1 | H | Cl |
| Ia.2 | F | Cl |
| Ia.3 | Cl | Cl |
| Ia.4 | H | Br |
| Ia.5 | F | Br |
| Ia.6 | Cl | Br |
| Ia.7 | H | I |
| Ia.8 | F | I |
| Ia.9 | Cl | I |
| Ia.10 | H | F |
| Ia.11 | F | F |
| Ia.12 | Cl | F |
| Ia.13 | H | H |
| Ia.14 | F | H |
| Ia.15 | Cl | H |
| Ia.16 | H | CH$_3$ |
| Ia.17 | F | CH$_3$ |
| Ia.18 | Cl | CH$_3$ |
| Ia.19 | H | CH$_2$CH$_3$ |
| Ia.20 | F | CH$_2$CH$_3$ |
| Ia.21 | Cl | CH$_2$CH$_3$ |
| Ia.22 | H | CH$_2$CH$_2$CH$_3$ |
| Ia.23 | H | CH$_2$CH$_2$CH$_3$ |
| Ia.24 | Cl | CH$_2$CH$_2$CH$_3$ |
| Ia.25 | H | CH(CH$_3$)$_2$ |

TABLE 2-continued

Ia

| No. | R⁴ | R⁶ |
|---|---|---|
| Ia.26 | F | CH(CH₃)₂ |
| Ia.27 | Cl | CH(CH₃)₂ |
| Ia.28 | H | CH₂CH₂CH₂CH₃ |
| Ia.29 | F | CH₂CH₂CH₂CH₃ |
| Ia.30 | Cl | CH₂CH₂CH₂CH₃ |
| Ia.31 | H | CHCH(CH₃)₂ |
| Ia.32 | F | CHCH(CH₃)₂ |
| Ia.33 | Cl | CHCH(CH₃)₂ |
| Ia.34 | H | C(CH₃)₃ |
| Ia.35 | F | C(CH₃)₃ |
| Ia.36 | H | C(CH₃)₃ |
| Ia.37 | H | CH(CH₃)CH₂CH₃ |
| Ia.38 | F | CH(CH₃)CH₂CH₃ |
| Ia.39 | Cl | CH(CH₃)CH₂CH₃ |
| Ia.40 | H | CH₂CH=CH₂ |
| Ia.41 | F | CH₂CH=CH₂ |
| Ia.42 | Cl | CH₂CH=CH₂ |
| Ia.43 | H | CH(CH₃)CH=CH₂ |
| Ia.44 | F | CH(CH₃)CH=CH₂ |
| Ia.45 | Cl | CH(CH₃)CH=CH₂ |
| Ia.46 | H | CH₂—CH=CH₂—CH₃ |
| Ia.47 | F | CH₂—CH=CH₂—CH₃ |
| Ia.48 | Cl | CH₂—CH=CH₂—CH₃ |
| Ia.49 | H | CH(CH₃)CH=CH—CH₃ |
| Ia.50 | F | CH(CH₃)CH=CH—CH₃ |
| Ia.51 | Cl | CH(CH₃)CH=CH—CH₃ |
| Ia.52 | H | CH₂C≡CH |
| Ia.53 | F | CH₂C≡CH |
| Ia.54 | Cl | CH₂C≡CH |
| Ia.55 | H | CH(CH₃)C≡CH |
| Ia.56 | F | CH(CH₃)C≡CH |
| Ia.57 | Cl | CH(CH₃)C≡CH |
| Ia.58 | H | CH₂C≡C—CH₃ |
| Ia.59 | F | CH₂C≡C—CH₃ |
| Ia.60 | Cl | CH₂C≡C—CH₃ |
| Ia.61 | H | CH₂Cl |
| Ia.62 | F | CH₂Cl |
| Ia.63 | Cl | CH₂Cl |
| Ia.64 | H | CH₂F |
| Ia.65 | F | CH₂F |
| Ia.66 | Cl | CH₂F |
| Ia.67 | H | CHF₂ |
| Ia.68 | F | CHF₂ |
| Ia.69 | Cl | CHF₂ |
| Ia.70 | H | CF₃ |
| Ia.71 | F | CF₃ |
| Ia.72 | Cl | CF₃ |
| Ia.73 | H | CClF₂ |
| Ia.74 | F | CClF₂ |
| Ia.75 | Cl | CClF₂ |
| Ia.76 | H | CCl₂F |
| Ia.77 | F | CCl₂F |
| Ia.78 | Cl | CCl₂F |
| Ia.79 | H | CH₂CHF₂ |
| Ia.80 | F | CH₂CHF₂ |
| Ia.81 | Cl | CH₂CHF₂ |
| Ia.82 | H | CH₂CH₂F |
| Ia.83 | F | CH₂CH₂F |
| Ia.84 | Cl | CH₂CH₂F |
| Ia.85 | H | CH₂CH₂Cl |
| Ia.86 | F | CH₂CH₂Cl |
| Ia.87 | Cl | CH₂CH₂Cl |
| Ia.88 | H | CH₂CH₂Br |
| Ia.89 | F | CH₂CH₂Br |
| Ia.90 | Cl | CH₂CH₂Br |
| Ia.91 | H | CH₂CH₂I |
| Ia.92 | F | CH₂CH₂I |
| Ia.93 | Cl | CH₂CH₂I |
| Ia.94 | H | CH₂CF₃ |
| Ia.95 | F | CH₂CF₃ |
| Ia.96 | Cl | CH₂CF₃ |
| Ia.97 | H | CF₂CF₃ |
| Ia.98 | F | CF₂CF₃ |
| Ia.99 | Cl | CF₂CF₃ |
| Ia.100 | H | CH₂CN |
| Ia.101 | F | CH₂CN |
| Ia.102 | Cl | CH₂CN |
| Ia.103 | H | CH(CH₃)CN |
| Ia.104 | F | CH(CH₃)CN |
| Ia.105 | Cl | CH(CH₃)CN |
| Ia.106 | H | CH₂CH₂CN |
| Ia.107 | F | CH₂CH₂CN |
| Ia.108 | Cl | CH₂CH₂CN |
| Ia.109 | H | CH(CH₃)CH₂CN |
| Ia.110 | F | CH(CH₃)CH₂CN |
| Ia.111 | Cl | CH(CH₃)CH₂CN |
| Ia.112 | H | CH₂CH₂OCH₃ |
| Ia.113 | F | CH₂CH₂OCH₃ |
| Ia.114 | Cl | CH₂CH₂OCH₃ |
| Ia.115 | H | CH₂CH₂OCH₂CH₃ |
| Ia.116 | F | CH₂CH₂OCH₂CH₃ |
| Ia.117 | Cl | CH₂CH₂OCH₂CH₃ |
| Ia.118 | H | CH(CH₃)CH₂OCH₃ |
| Ia.119 | F | CH(CH₃)CH₂OCH₃ |
| Ia.120 | Cl | CH(CH₃)CH₂OCH₃ |
| Ia.121 | H | CH(CH₃)CH₂OCH₂CH₃ |
| Ia.122 | F | CH(CH₃)CH₂OCH₂CH₃ |
| Ia.123 | Cl | CH(CH₃)CH₂OCH₂CH₃ |
| Ia.124 | H | CH₂COOCH₃ |
| Ia.125 | F | CH₂COOCH₃ |
| Ia.126 | Cl | CH₂COOCH₃ |
| Ia.127 | H | CH₂COOCH₂CH₃ |
| Ia.128 | F | CH₂COOCH₂CH₃ |
| Ia.129 | Cl | CH₂COOCH₂CH₃ |
| Ia.130 | H | CH₂COOCH(CH₃)₂ |
| Ia.131 | F | CH₂COOCH(CH₃)₂ |
| Ia.132 | Cl | CH₂COOCH(CH₃)₂ |
| Ia.133 | H | CH(CH₃)COOCH₃ |
| Ia.134 | F | CH(CH₃)COOCH₃ |
| Ia.135 | Cl | CH(CH₃)COOCH₃ |
| Ia.136 | H | CH(CH₃)COOCH₂CH₃ |
| Ia.137 | F | CH(CH₃)COOCH₂CH₃ |
| Ia.138 | Cl | CH(CH₃)COOCH₂CH₃ |
| Ia.139 | H | CH(CH₃)COOCH(CH₃)₂ |
| Ia.140 | F | CH(CH₃)COOCH(CH₃)₂ |
| Ia.141 | Cl | CH(CH₃)COOCH(CH₃)₂ |
| Ia.142 | H | CH₂CH₂COOCH₃ |
| Ia.143 | F | CH₂CH₂COOCH₃ |
| Ia.144 | Cl | CH₂CH₂COOCH₃ |
| Ia.145 | H | CH₂CH₂COOCH₂CH₃ |
| Ia.146 | F | CH₂CH₂COOCH₂CH₃ |
| Ia.147 | Cl | CH₂CH₂COOCH₂CH₃ |
| Ia.148 | H | CH(CH₂CH₃)COOCH₃ |

TABLE 2-continued

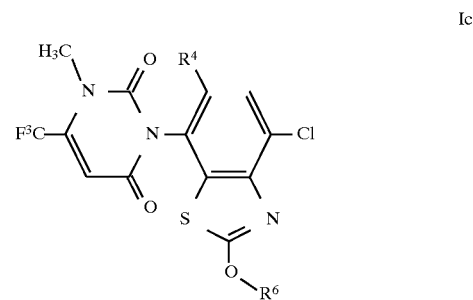

Ia

| No. | R⁴ | R⁶ |
|---|---|---|
| Ia.149 | F | CH(CH₂CH₃)COOCH₃ |
| Ia.150 | Cl | CH(CH₂CH₃)COOCH₃ |
| Ia.151 | H | CH(CH₂CH₃)COOCH₂CH₃ |
| Ia.152 | F | CH(CH₂CH₃)COOCH₂CH₃ |
| Ia.153 | Cl | CH(CH₂CH₃)COOCH₂CH₃ |
| Ia.154 | H | CH[CH(CH₃)₂]COOCH₃ |
| Ia.155 | F | CH[CH(CH₃)₂]COOCH₃ |
| Ia.156 | Cl | CH[CH(CH₃)₂]COOCH₃ |
| Ia.157 | H | CH₂CH₂OCOCH₃ |
| Ia.158 | F | CH₂CH₂OCOCH₃ |
| Ia.159 | Cl | CH₂CH₂OCOCH₃ |
| Ia.160 | H | CH₂CH₂OCOCH₂CH₃ |
| Ia.161 | F | CH₂CH₂OCOCH₂CH₃ |
| Ia.162 | Cl | CH₂CH₂OCOCH₂CH₃ |
| Ia.163 | H | CH(CH₃)CH₂OCOCH₃ |
| Ia.164 | F | CH(CH₃)CH₂OCOCH₃ |
| Ia.165 | Cl | CH(CH₃)CH₂OCOCH₃ |
| Ia.166 | H | CH₂CH(CH₃)OCOCH₃ |
| Ia.167 | F | CH₂CH(CH₃)OCOCH₃ |
| Ia.168 | Cl | CH₂CH(CH₃)OCOCH₃ |
| Ia.169 | H | CH₂CH₂OCHF₂ |
| Ia.170 | F | CH₂CH₂OCHF₂ |
| Ia.171 | Cl | CH₂CH₂OCHF₂ |
| Ia.172 | H | CH₂CH₂OCH₂CF₃ |
| Ia.173 | F | CH₂CH₂OCH₂CF₃ |
| Ia.174 | Cl | CH₂CH₂OCH₂CF₃ |
| Ia.175 | H | cyclohexyl |
| Ia.176 | F | cyclohexyl |
| Ia.177 | Cl | cyclohexyl |
| Ia.178 | H | CH=CH—COOCH₃ |
| Ia.179 | F | CH=CH—COOCH₃ |
| Ia.180 | Cl | CH=CH—COOCH₃ |
| Ia.181 | H | CH=CH—COOCH₂CH₃ |
| Ia.182 | F | CH=CH—COOCH₂CH₃ |
| Ia.183 | Cl | CH=CH—COOCH₂CH₃ |
| Ia.184 | H | CN |
| Ia.185 | F | CN |
| Ia.186 | Cl | CN | furthermore, the following substituted benzothiazoles of the formulae Ib to Iu are vary particularly preferred, in particular:

the compounds Ib.1 to Ib.186, which differ from the compounds Ia.1 to Ia.186 only in that R¹ is amino:

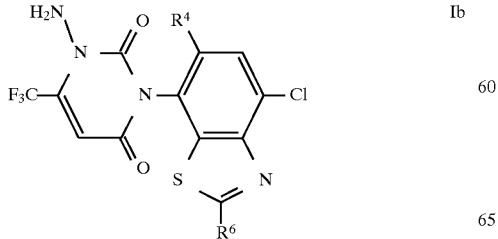

Ib the compounds Ic.13 to Ic.186, which differ from the compounds Ia.13 to Ia.186 only in that Y is oxygen:

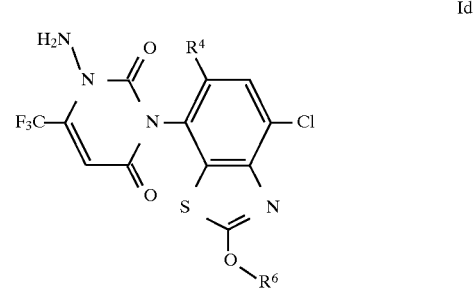

Ic the compounds Id.13 to Id.186, which differ from the compounds Ia.13 to Ia.186 only in that R¹ is amino and Y is oxygen:

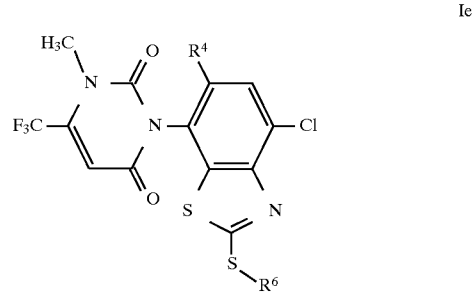

Id the compounds Ie.13 to Ie.186, which differ from the compounds Ia.13 to Ia.186 only in that Y is sulfur:

Ie the compounds If.13 to If.186, which differ from the compounds Ia.13 to Ia.186 only in that R¹ is amino and Y is sulfur:

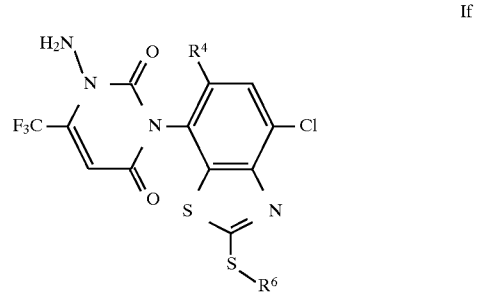

If the compounds Ig.13 to Ig.183, which differ from the compounds Ia.13 to Ia.183 only in that Y is —SO—:

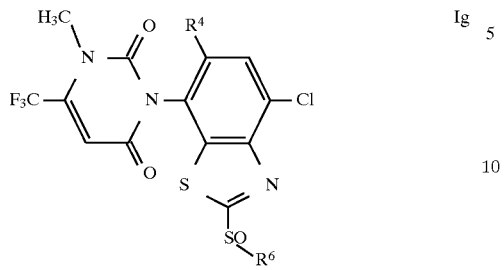

the compounds Ih.13 to Ih.183, which differ from the compounds Ia.13 to Ia.183 only in that $R^1$ is amino and Y is —SO—:

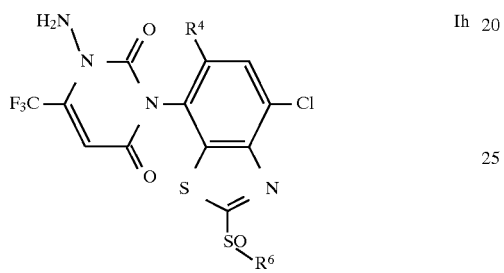

the compounds Ii.13 to Ii.183, which differ from the compounds Ia.13 to Ia.183 only in that Y is —SO$_2$—:

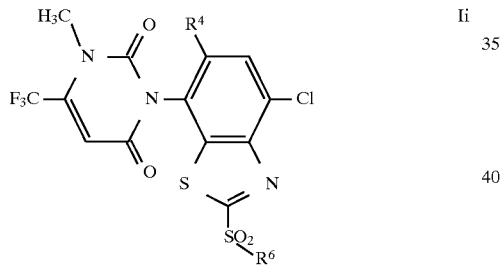

the compounds Ik.13 to Ik.183, which differ from the compounds Ia.13 to Ia.183 only in that $R^1$ is amino and Y is —SO$_2$—:

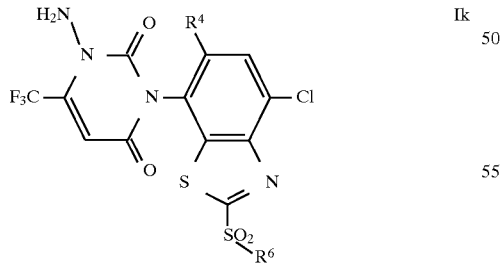

the compounds Il.1 to Il.186, which differ from the compounds Ia.1 to Ia.186 only in that $R^5$ is cyano:

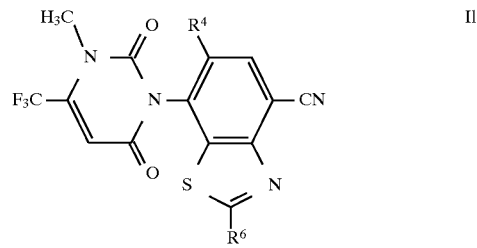

the compounds Im.1 to Im.186, which differ from the compounds Ia.1 to Ia.186 only in that $R^1$ is amino and $R^5$ is cyano:

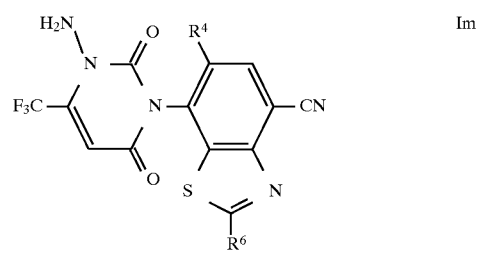

the compounds In.13 to In.186, which differ from the compounds Ia.13 to Ia.186 only in that Y is oxygen and $R^5$ is cyano:

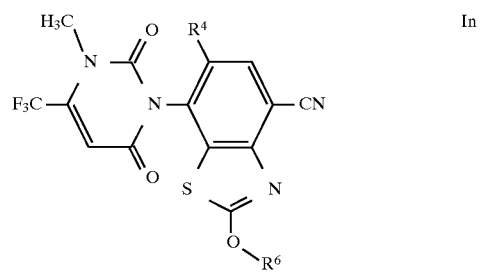

the compounds Io.13 to Io.186, which differ from the compounds Ia.13 to Ia.186 only in that $R^1$ is amino, $R^5$ is cyano and Y is oxygen:

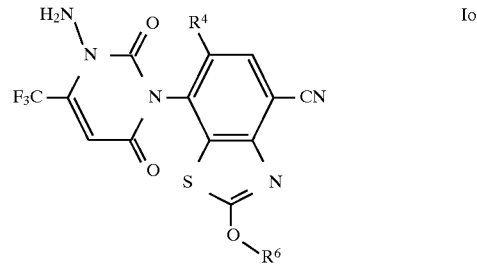

the compounds Ip.13 to Ip.186, which differ from the compounds Ia.13 to Ia.186 only in that Y is sulfur and $R^5$ is cyano:

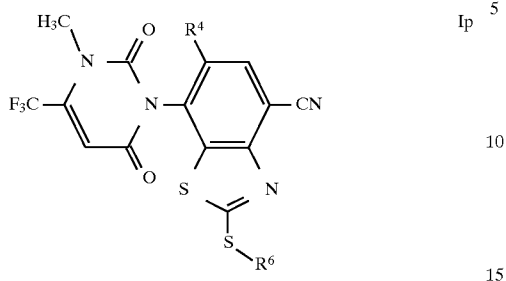

the compounds Iq.13 to Iq.186, which differ from the is compounds Ia.13 to Ia.186 only in that $R^1$ is amino, $R^5$ is cyano and Y is sulfur:

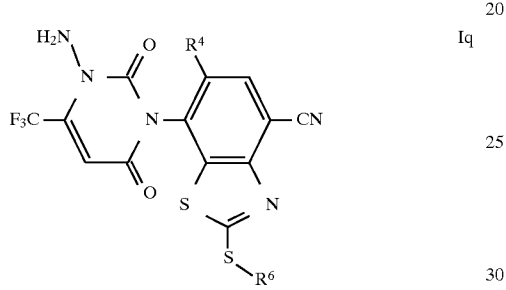

the compounds Ir.13 to Ir.183, which differ from the compounds Ia.13 to Ia.183 only in that Y is —So— and $R^5$ is cyano:

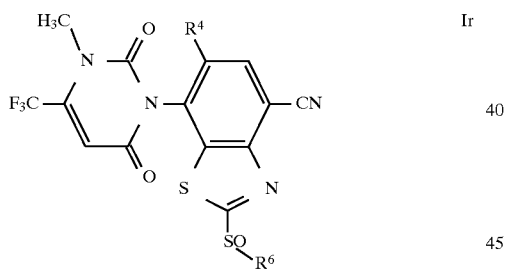

the compounds Is.13 to Is.183, which differ from the compounds Ia.13 to Ia.183 only in that $R^1$ is amino, $R^5$ is cyano and Y is —SO—:

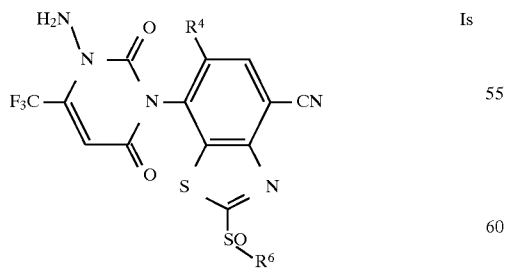

the compounds It.13 to It.183, which differ from the compounds Ia.13 to Ia.183 only in that $R^5$ is cyano and Y is —$SO_2$—:

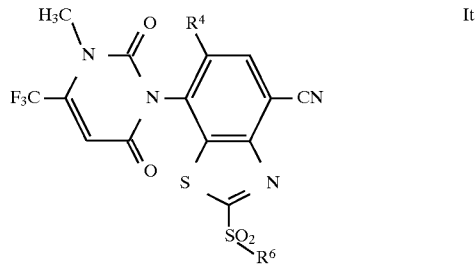

the compounds Iu.13 to Iu.183, which differ from the compounds Ia.13 to Ia.183 only in that $R^1$ is amino, $R^5$ is cyano and Y is —$SO_2$—:

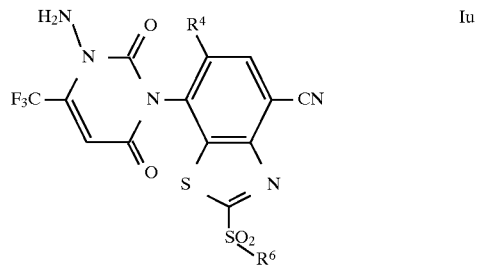

The substituted benzothiazoles of the formula I are obtainable by various methods, for example by one of the following processes:

Process A)

Reaction of a substituted benzothiazole I in which $R^1$ is hydrogen with a compound II in a manner known per se:

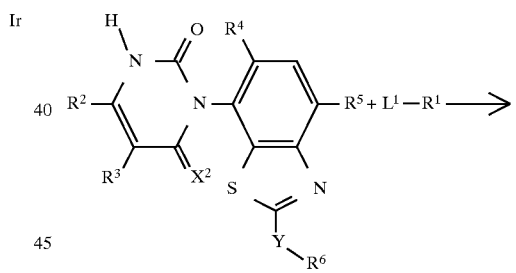

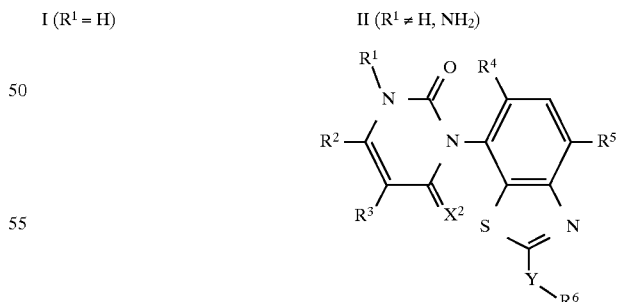

$L^1$ is a conventional leaving group, such as halogen, preferably chlorine, bromine or iodine, (halo)

alkylsulfonyloxy, preferably methylsulfonyloxy or trifluoromethylsulfonyloxy, arylsulfonyloxy, preferably toluenesulfonyloxy, or alkoxysulfonyloxy, preferably methoxysulfonyloxy or ethoxysulfonyloxy.

The reaction is usually carried out in an inert organic solvent, for example in a protic solvent, such as the lower alcohols, preferably methanol or ethanol, if desired as a mixture with water, or in an aprotic solvent, for example in an aliphatic or cyclic ether, such as methyl tert-butyl ether, 1,2-dimethoxyethane, tetrahydrofuran and dioxane, in an aliphatic ketone, such as acetone, diethyl ketone or ethyl methyl ketone, in an amide, such as dimethylformamide or N-methylpyrrolidone, in a sulfoxide, such as dimethyl sulfoxide, in a urea, such as tetramethylurea or 1,3-dimethyltetrahydro-2(1H)-pyrimidinone, in a carboxylic ester, such as ethyl acetate, or in a halogenated aliphatic or aromatic hydrocarbon, such as dichloromethane, dichloroethane, chlorobenzene or a dichlorobenzene.

If desired, the reaction may be carried out in the presence of a base, both inorganic bases, for example carbonates, such as sodium carbonate and potassium carbonate, bicarbonates, such as sodium bicarbonate and potassium bicarbonate, or alkali metal hydrides, such as sodium hydride and potassium hydride, and organic bases, for example amines, such as triethylamine, pyridine and N,N-diethylaniline, or alkali metal alcoholates, such as sodium methylate, sodium ethylate and potassium tert-butylate, being suitable.

The amount of base and alkylating agent II is in each case preferably from 0.5 times to twice the molar amount, based on the amount of starting compound I (where $R^1$ is hydrogen). In general, the reaction temperature is from 0° C. to the boiling point of the reaction mixture, in particular from 0° to 60° C.

In a preferred process variant, the salt of I, which salt is obtained from the cyclization of IV where $R^1$ is H or V where $R^1$ is H according to process G), is alkylated, without isolation from the reaction mixture—which may also contain excess base, eg. sodium hydride, sodium alcoholate or sodium carbonate.

Unless they can be prepared directly by the cyclization under basic conditions, described as method G), the salts of those compounds I in which $R^1$ is hydrogen can also be obtained in a manner known per se from the products of methods D) to I). For this purpose, for example, the substituted benzothiazole I in which $R^1$ is hydrogen is added to the aqueous solution of an inorganic or organic base. Salt formation then usually takes place at a sufficient rate at as low as from 20° to 25° C.

It is particularly advantageous to prepare the sodium salt by dissolving the substituted benzothiazole I, where $R^1$ is hydrogen, in an aqueous sodium hydroxide solution at from 20° to 25° C., about equivalent amounts of benzothiazole I (where $R^1$ is H) and sodium hydroxide being used. The corresponding salt of the benzothiazole I can then be isolated, for example by precipitation with a suitable inert solvent or by evaporating off the solvent.

Salts of the substituted benzothiazoles I whose metal ion is not an alkali metal ion can usually be prepared by double decomposition of the corresponding alkali metal salt in aqueous solution, as can ammonium, phosphonium, sulfonium and sulfoxonium salts by means of ammonia or phosphonium, sulfonium or sulfoxonium hydroxides. For example, benzothiazole metal salts which are insoluble in water can be prepared in this manner.

Process B)

Reaction of a substituted benzothiazole of the formula I, where $R^1$ is hydrogen, with an electrophilic aminating reagent in the presence of a base:

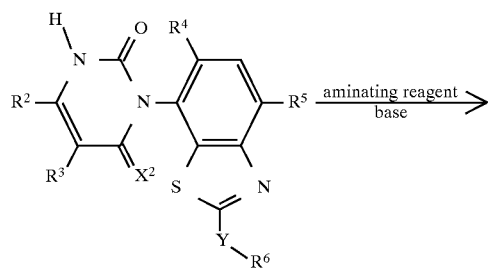

I ($X^1$ = O; $R^1$ = H)

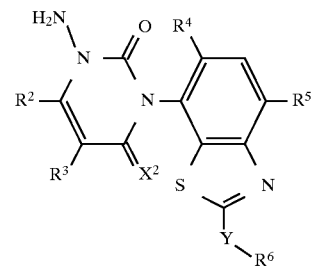

I ($X^1$ = O; $R^1$ = NH$_2$)

2,4-Dinitrophenoxyamine has proven particularly useful to date as an aminating reagent, but, for example, hydroxylamine-O-sulfonic acid (HOSA) may also be used and is known as an aminating reagent in the literature (cf. for example E. Hofer et al., Synthesis 1983, 466; W. Friedrichsen et al., Heterocycles 20 (1983) 1271; H. Hart et al., Tetrahedron Lett. 25 (1984) 2073; B. Vercek et al., Monatsh. Chem. 114 (1983) 789; G. Sosnousky et al., Z. Naturforsch. 38 (1983) 884; R. S. Atkinson et al., J. Chem. Soc. Perkin Trans. 1987, 2787).

The amination can be carried out in a manner known per se (cf. for example T. Sheradsky, Tetrahedron Lett. 1968, 1909; M. P. Wentland et al., J. Med. Chem. 27 (1984) 1103 and in particular EP-A 240 194, EP-A 476 697 and EP-A 517 181, where the amination of uracils is described).

The reaction is usually carried out in a polar solvent, for example in dimethylformamide, N-methylpyrrolidone or dimethyl sulfoxide or in ethyl acetate, which has to date proven particularly suitable.

Examples of suitable bases are alkali metal carbonates, such as potassium carbonate, alkali metal alcoholates, such as sodium methylate and potassium tert-butylate, and alkali metal hydrides, such as sodium hydride.

The amount of base and aminating agent is in each case preferably from 0.5 times to twice the molar amount, based on the amount of starting compound.

Process C)

Sulfurization of a substituted benzothiazole of the formula I, where $X^2$ is oxygen:

I ($X^1$, $X^2$ = O)  $\xrightarrow{\text{sulfurization}}$  I ($X^1$ = O; $X^2$ = S)

I ($X^1$, $X^2$ = O; Y = O, S)

The sulfurization is carried out, as a rule, in an inert solvent or diluent, for example in an aromatic hydrocarbon, such as toluene or one of the xylenes, in an ether, such as diethyl ether, 1,2-dimethoxyethane and tetrahydrofuran, or in an organic amine, such as pyridine.

Particularly suitable sulfurization reagents are phosphorus (V) sulfide and 2,4-bis(4-methoxyphenyl)-1,3,2,4-dithiadiphosphetane-2,4-dithione (Lawesson's reagent).

From 1 to 5 times the molar amount, based on the starting compound to be sulfurized, is usually sufficient for a substantially complete reaction.

The reaction temperature is usually from 20° to 200° C., preferably from 40° C. to the boiling point of the reaction mixture.

Process D)

Reaction of a substituted benzothiazole I in which —$YR^6$ is chlorine, bromine, alkylsulfonyl or haloalkylsulfonyl in a manner known per se with an alcohol or mercaptan III in the presence of a base:

I ($X^1$, $X^2$ = O; —$YR^6$ = Cl, Br, —$SO_2$-alkyl, —$SO_2$-haloalkyl) + $HOR^6$ or $HSR^6$ $\xrightarrow{\text{base}}$ Reaction is advantageously carried out in an inert solvent, for example in an ether, such as diethyl ether, methyl-tert-butyl ether, dimethoxyethane, diethylene glycol dimethyl ether, tetrahydrofuran or dioxane, a ketone, such as acetone, diethyl ketone, ethyl methyl ketone or cyclohexanone, a dipolar aprotic solvent, such as acetonitrile, dimethylformamide, N-methylpyrrolidone or dimethyl sulfoxide, a protic solvent, such as methanol or ethanol, an aromatic hydrocarbon which if desired may be halogenated, such as benzene, chlorobenzene or 1,2-dichlorobenzene, a heteroaromatic solvent, such as pyridine or quinoline, or a mixture of such solvents. Tetrahydrofuran, acetone, diethyl ketone and dimethylformamide are preferred.

The bases used here may be, for example, the hydroxides, hydrides, alkoxides, carbonates or bicarbonates of alkali metal and alkaline earth metal cations, tertiary aliphatic amines, such as triethylamine, N-methylmorpholine and N-ethyl-N,N-diisopropylamine, bi- and tricyclic amines, such as diazabicycloundecane (DBU) and diazabicyclooctane (DABCO), or aromatic nitrogen bases, such as pyridine, 4-dimethylaminopyridine and quinoline. Combinations of different bases are also suitable. Preferred bases are sodium hydride, sodium hydroxide, sodium carbonate, potassium carbonate, sodium methylate, sodium ethylate and potassium tert-butylate.

The starting materials are usually used in roughly stoichiometric amounts, but an excess of one or other component may also be advantageous with regard to the procedure or for as complete conversion as possible of the starting compound I ($X^1$ and $X^2$=O; —$YR^6$=Cl, Br, —$SO_2$-alkyl or —$SO_2$-haloalkyl).

The molar ratio of alcohol or mercaptan III to base is in general from 1:1 to 1:3.

The concentration of the starting materials in the solvent is usually from 0.1 to 5.0 mol/l.

The reaction can be carried out at from 0° C. to the reflux temperature of the respective solvent (mixture).

Process E)

Oxidation of a substituted benzothiazole I in which Y is sulfur to give I where Y is —SO— in a manner known per se (cf. for example Houben-Weyl, Methoden der Organischen Chemie, Georg Thieme Verlag Stuttgart, vol. E 11/1, 1985, page 702 et seq., vol. IX, 4th edition, 1955, page 211):

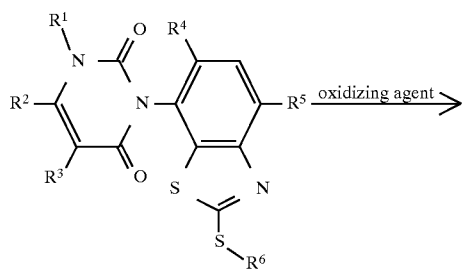

I (X$^1$, X$^2$ = O; Y = S)

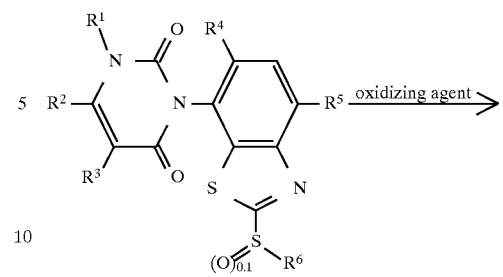

I (X$^1$, X$^2$ = O; Y = S, SO)

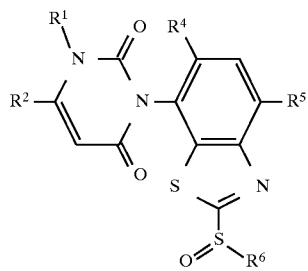

I (X$^1$, X$^2$ = O; Y = SO)

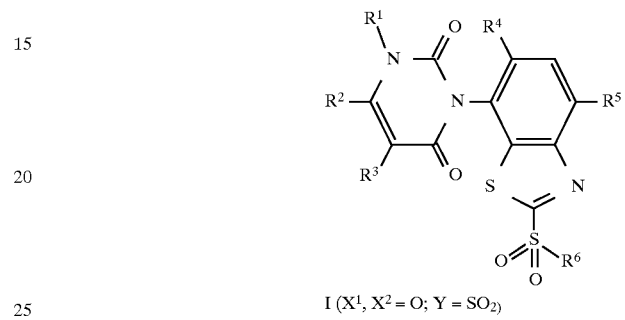

I (X$^1$, X$^2$ = O; Y = SO$_2$)

Suitable oxidizing agents are, for example, hydrogen peroxide, organic peroxides, such as peroxyacetic acid, peroxytrifluoroacetic acid, m-chloroperbenzoic acid, tert-butyl hydroperoxide and tert-butyl hypochlorite, and inorganic compounds, such as sodium metaiodate, chromic acid and nitric acid.

Depending on the oxidizing agent, the reaction is usually carried out in an organic acid, such as acetic acid or trichloroacetic acid, in a chlorinated hydrocarbon, such as methylene chloride, chloroform or 1,2-dichloroethane, in an aromatic hydrocarbon, such as benzene, chlorobenzene or toluene, or in a protic solvent, such as methanol or ethanol. Mixtures of the stated solvents are also suitable.

The reaction temperature is in general from −30° C. to the boiling point of the respective reaction mixture, the lower temperature range usually being preferred.

The starting compound and oxidizing agent are advantageously used in a roughly stoichiometric ratio, but one or other component may also be employed in excess.

Process F)

Oxidation of a substituted benzothiazole I in which Y is sulfur or —SO— to give I where Y is —SO$_2$— in a manner known per se (cf. for example Houben-Weyl, Methoden der Organischen Chemie, Georg Thieme Verlag Stuttgart, vol. E 11/2, 1985, page 1132 et seq., and vol. IX, 4th edition, 1955, page 222 et seq.):

Suitable oxidizing agents are, for example, hydrogen peroxide, organic peroxides, such as peroxyacetic acid, peroxytrifluoroacetic acid and m-chloroperbenzoic acid, and inorganic oxidizing agents, such as potassium permanganate. The presence of a catalyst, for example tungstate, may promote the reaction.

As a rule, the reaction is carried out in an inert solvent; depending on the oxidizing agent, for example, organic acids, such as acetic acid and propionic acid, chlorinated hydrocarbons, such as methylene chloride, chloroform and 1,2-dichloroethane, aromatic hydrocarbons and halohydrocarbons, such as benzene, chlorobenzene and toluene, and water may be used. Mixtures of the stated solvents are also suitable.

The reaction is usually carried out from −30° C. to the boiling point of the respective reaction mixture, preferably from 10° C. to the boiling point.

The starting compound I where Y is S or SO and the oxidizing agent are advantageously used in roughly stoichiometric amounts. However, an excess of oxidizing agent may be advisable for optimizing the conversion of starting compounds.

Process G)

Cyclization of an enamine ester of the formula IV or of an enamine carboxylate of the formula V in the presence of a base:

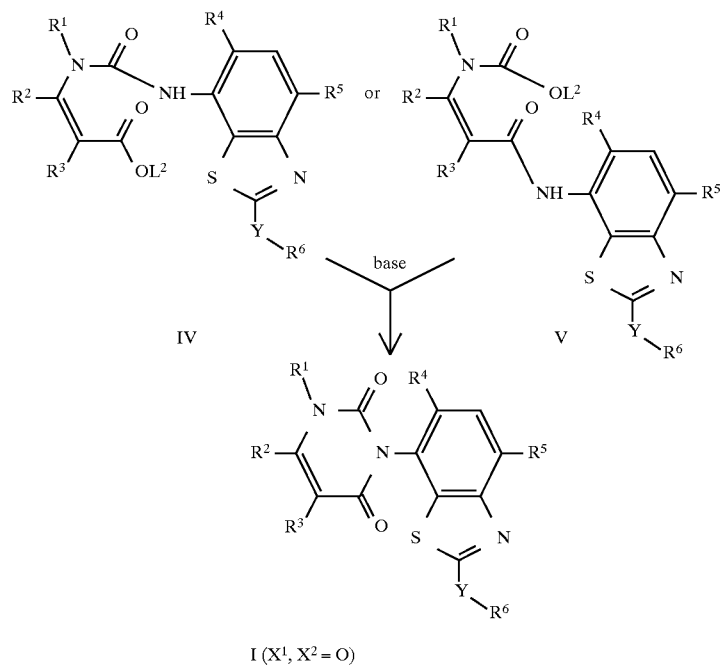

I (X¹, X² = O)

$L^2$ is low molecular weight alkyl, preferably $C_1$–$C_4$-alkyl, or phenyl.

As a rule, the cyclization is carried out in an inert organic solvent or diluent which is aprotic, for example in an aliphatic or cyclic ether, such as 1,2-dimethoxyethane, tetrahydrofuran or dioxane, in an aromatic, such as benzene or toluene, or in a polar solvent, such as dimethylformamide or dimethyl sulfoxide. Mixtures of polar solvent and a hydrocarbon, such as n-hexane, are also suitable. Depending on the starting compound, water may also be used as a diluent.

Preferred bases are alkali metal alcoholates, in particular the sodium alcoholates, alkali metal hydroxides, in particular sodium hydroxide and potassium hydroxide, alkali metal carbonates, in particular sodium carbonate and potassium carbonate, and metal hydrides, in particular sodium hydride. Where sodium hydride is used as the base, it has proven advantageous to carry out the reaction in an aliphatic or cyclic ether, in dimethylformamide or in dimethyl sulfoxide.

From 0.5 times to twice the molar amount, based on the amount of IV or V, of base is usually sufficient for carrying out the reaction successfully.

In general, the reaction temperature is from −78° C. to the boiling point of the respective reaction mixture, in particular from −60° to 60° C.

If $R^1$ is hydrogen in the formula IV or V, the product is obtained as a metal salt, the metal corresponding to the cation of the base used. The salt can be isolated and purified in a manner known per se or, if desired, converted into the free compound I, where $R^1$ is hydrogen, by means of an acid.

Process H)

Conversion of a 2-aminobenzothiazole of the formula VI into compounds of the formula I where —YR⁶ is halogen, cyano, thiocyanato or cyanato by the Sandmeyer method or a variant thereof:

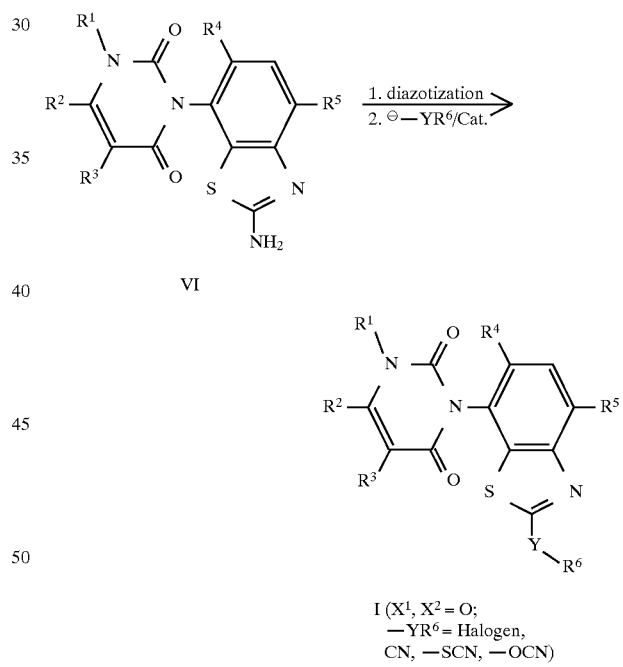

I (X¹, X² = O; —YR⁶ = Halogen, CN, —SCN, —OCN)

In this type of reaction, the 2-aminobenzothiazole VI is first converted into a diazonium salt, this being advantageously effected in a manner known per se by reacting the 2-aminobenzothiazole VI with a nitrite, such as sodium nitrite or potassium nitrite, in an aqueous acid solution—for example in aqueous hydrochloric acid, hydrobromic acid or sulfuric acid.

The diazonium salt thus obtained can then be reacted, without further purification, with a corresponding acid HYR⁶, such as hydrochloric acid or hydrobromic acid, or with a corresponding metal salt of HYR⁶, such as lithium, sodium or potassium chloride, lithium, sodium or potassium bromide, lithium, sodium or potassium cyanide or lithium, sodium or potassium thiocyanate, in the presence of a transition metal catalyst, in particular of a copper(I) salt, such as copper(I) chloride, copper(I) bromide, copper(I) cyanide, copper(I) thiocyanate or copper(I) cyanate.

A further possibility for the preparation of the diazonium salt of the benzothiazole VI is to react VI with an ester of nitrous acid, such as tert-butyl nitrite or isopropyl nitrite, in an anhydrous system—for example in glacial acetic acid which contains hydrogen chloride, or in dioxane, absolute ethanol, tetrahydrofuran, acetonitrile or acetone. In this case, the diazotization can take place in the presence of a transition metal catalyst and of the corresponding metal salt of —$YR^6$, as described above.

The reaction temperature is usually from −30° to 80° C.

Usually, the components of the diazotization reaction are used in roughly stoichiometric amounts, but an excess of one of the components may also be advantageous, for example for achieving as complete conversion as possible of one of the other components.

The transition metal catalyst may be used in less than the stoichiometric amount, in a roughly equimolar amount or in excess, and the acids and the metal salts may be used either in roughly equimolar amounts or, preferably, in a large excess.

Process I)

conversion of a 2-aminobenzothiazole of the formula VI into compounds of the formula I where Y is sulfur by mercapto dediazotization:

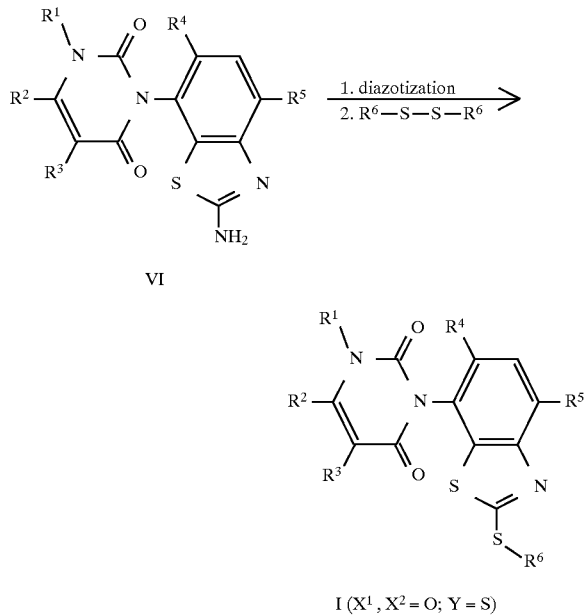

For this purpose, the 2-aminobenzothiazole VI is converted into the corresponding diazonium salt of the benzothiazole in an anhydrous system—for example an ether, such as dioxane or tetrahydrofuran, a nitrile, such as acetonitrile, or a halohydrocarbon, such as methylene chloride or 1,2-dichloroethane—with an ester of nitrous acid, such as tert-butyl nitrite or isopropyl nitrite. Said diazonium salt is then reacted with the corresponding disulfide $R^6$—SS—$R^6$. However, the diazotization itself may also be carried out in the presence of the disulfide.

The reaction is usually carried out at from −30° to 80° C.

The reactants are advantageously used in roughly stoichiometric amounts, unless an excess of one or more of the components is advisable, for example to achieve as complete conversion as possible of VI.

Substituted benzothiazoles of the formula I having one or more centers of chirality are usually obtained as enantiomer or diastereomer mixtures, which, if desired, may be separated into the substantially pure isomers by the conventional methods, for example by means of crystallization or chromatography over an optically active adsorbate. Pure optically active isomers can also be prepared, for example, from corresponding optically active starting materials.

Those substituted benzothiazoles of the formula I in which $R^1$ is hydrogen can be converted into their salts in a manner known per se (in this context, cf. the statements under process A)).

The enamine esters of the formula IV are novel. Their preparation can be carried out by methods known per se, for example by one of the following processes:

Process K)

Reaction of a β-ketocarboxylic ester VII with a urea VIII:

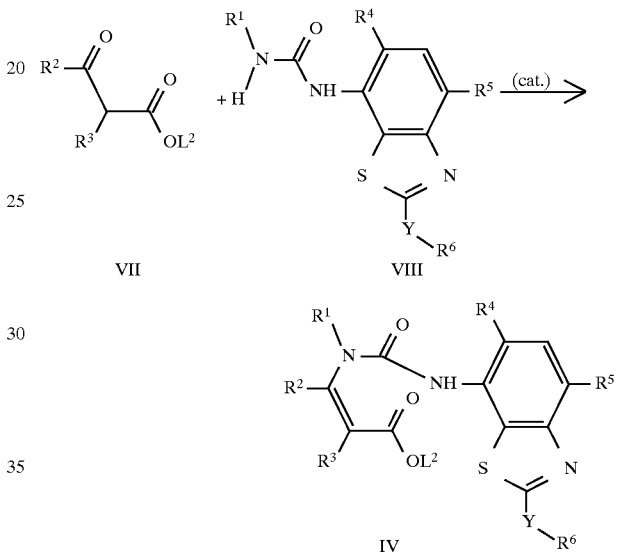

$L^2$ is low molecular weight alkyl, preferably $C_1$–$C_4$-alkyl, or phenyl.

The reaction was preferably carried out under essentially anhydrous conditions in an inert solvent or diluent, particularly preferably in the presence of an acidic or basic catalyst.

Particularly suitable solvents or diluents are organic solvents capable of forming an azeotropic mixture with water, for example aromatics, such as benzene, toluene and o-, m- and p-xylene, halogenated hydrocarbons, such as methylene chloride, chloroform, carbon tetrachloride and chlorobenzene, aliphatic and cyclic ethers, such as 1,2-dimethoxyethane, tetrahydrofuran and dioxane, and cyclohexane, as well as alcohols, such as methanol and ethanol.

Preferred acidic catalysts are strong mineral acids, such as sulfuric acid and hydrochloric acid, phosphorus-containing acids, such as orthophosphoric acid and polyphosphoric acid, organic acids, such as p-toluenesulfonic acid, and acidic cation exchangers, such as Amberlyst 15 (from Fluka).

Suitable basic catalysts are, for example, alkali metal hydrides, such as sodium hydride, and particularly preferably alkali metal alcoholates, such as sodium methylate and ethylate.

Advantageously, VIII and the β-ketocarboxylic esters VII are used in roughly stoichiometric amounts, or the reaction is carried out with a slight excess, up to about 10 mol %, of one or other component.

From 0.5 to 2 mol %, based on the amount of one of the starting compounds, of catalyst are usually sufficient.

In general, the reaction is carried out at from 60° to 120° C., or, for rapid removal of water formed, preferably at the boiling point of the reaction mixture.

Process L)

Reaction of an enol ether IX with a urea VIII:

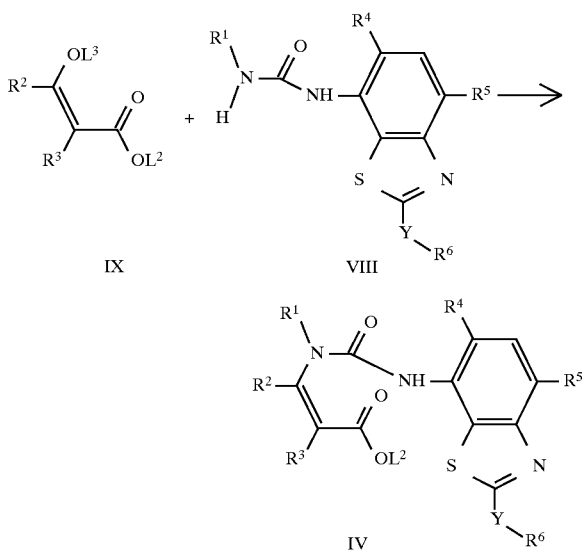

$L^2$ and $L^3$ are each low molecular weight alkyl, preferably $C_1$–$C_4$-alkyl, or phenyl.

The reaction is preferably carried out in an inert, water-miscible, organic solvent, for example an aliphatic or cyclic ether, such as 1,2-dimethoxyethane, tetrahydrofuran or dioxane, or a lower alcohol, in particular ethanol, the reaction temperature usually being from 50° to 100° C., preferably at the boiling point of the reaction mixture.

However, the reaction can also be carried out in an aromatic diluent, such as benzene, toluene or o-, m- or p-xylene, the addition of either an acidic catalyst, such as hydrochloric acid or p-toluenesulfonic acid, or a base, for example an alkali metal alcoholate, such as sodium methylate or sodium ethylate, being advisable in this case. In this process variant, too, the reaction temperature is usually from 50° to 100° C., preferably from 60° to 80° C.

The information provided for method K) is applicable with regard to the ratios.

Process M)

Reaction of an enaminoester X with an isocyanate XI:

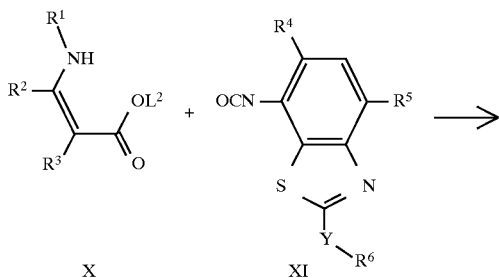

$L^2$ is lower molecular weight alkyl, preferably $C_1$–$C_4$-alkyl, or phenyl.

The reaction is advantageously carried out in the presence of an essentially anhydrous aprotic organic solvent or diluent, for example an aliphatic or cyclic ether, such as diethyl ether, 1,2-dimethoxyethane, tetrahydrofuran or dioxane, an aliphatic or aromatic hydrocarbon, such as n-hexane, benzene, toluene or o-, m- or p-xylene, a halogenated, aliphatic hydrocarbon, such as methylene chloride, chloroform, carbon tetrachloride, 1,2-dichloroethane or chlorobenzene, an aprotic, polar solvent, such as dimethylformamide, hexamethylphosphorotriamide or dimethyl sulfoxide, or a mixture of the stated solvents.

If desired, the reaction may also be carried out in the presence of a metal hydride base, such as sodium hydride or potassium hydride, or an organic tertiary base, such as triethylamine or pyridine, and the organic base may simultaneously serve as the solvent.

The starting materials are advantageously used in stoichiometric amounts or the reaction is carried out with a slight excess, up to about 10 mol %, of one or other component. If the reaction is carried out in the absence of a solvent and in the presence of an organic base, the latter is present in a relatively large excess.

The reaction temperature is preferably from –80° to 50° C., in particular from –60° to 30° C.

In a particularly preferred embodiment, the enaminoester IV obtained is reacted directly (ie. in situ) with excess base according to process G) to give the corresponding desired product I.

Process N)

Reaction of an enaminoester X with a urethane XII:

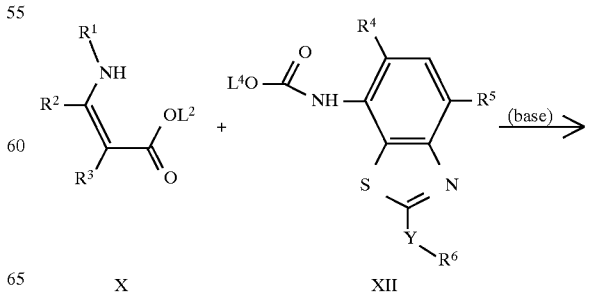

-continued

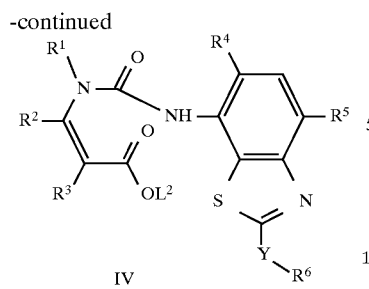

IV $L^2$ and $L^4$, independently of one another, are each low molecular weight alkyl, preferably $C_1$–$C_4$-alkyl, or phenyl.

This reaction is advantageously carried out in an aprotic, polar solvent or diluent, such as dimethylformamide, 2-butanone, dimethyl sulfoxide or acetonitrile, and advantageously in the presence of a base, for example of an alkali metal alcoholate or alkaline earth metal alcoholate, in particular of a sodium alcoholate, such as sodium methylate, an alkali metal carbonate or alkaline earth metal carbonate, in particular sodium carbonate, or an alkali metal hydride, such as lithium hydride or sodium hydride.

The molar amount or twice the molar amount, based on the amount of X or XII, of base is usually sufficient.

The reaction temperature is in general from 80° to 180° C., preferably the boiling point of the reaction mixture.

The information provided for method K) is applicable with regard to the ratios of the starting compounds.

In a particularly preferred embodiment, a sodium alcoholate is used as the base, and the alcohol formed in the course of the reaction is continuously distilled off. The enaminoesters IV prepared in this manner can, without isolation from the reaction mixture, be cyclized according to process G) to give a salt of the substituted benzothiazoles I (where $R^1$ is H).

Process O)

Reaction of an isocyanate XIII with an aniline derivative XIV:

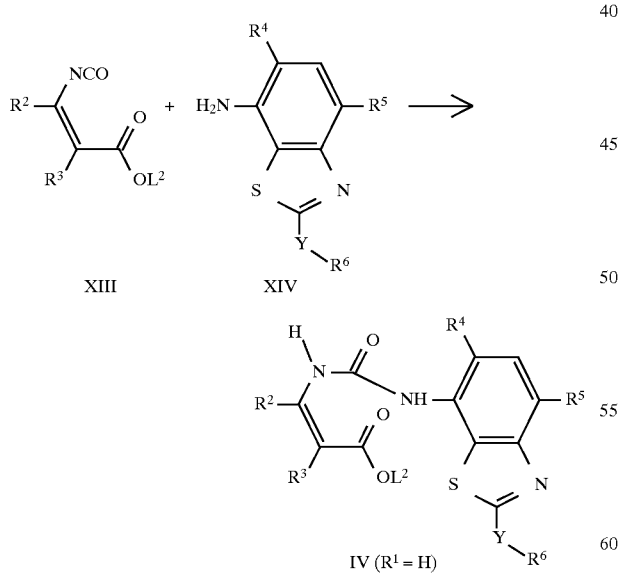

$L^2$ is low molecular weight alkyl, preferably $C_1$–$C_4$-alkyl, or phenyl.

This reaction is advantageously carried out in an essentially anhydrous, aprotic, organic solvent or diluent, for example in the presence of an aliphatic or cyclic ether, such as diethyl ether, 1,2-dimethoxyethane, tetrahydrofuran or dioxane, an aliphatic or aromatic hydrocarbon, such as n-hexane, benzene, toluene or o-, m- or p-xylene, a halogenated, aliphatic hydrocarbon, such as methylene chloride, chloroform, carbon tetrachloride, 1,2-dichloroethane or chlorobenzene, an aprotic, polar solvent, such as dimethylformamide, hexamethylphos- phorotriamide or dimethyl sulfoxide, or a mixture of the stated solvents.

If desired, the reaction may be carried out in the presence of a metal hydride base, such as sodium hydride or potassium hydride, an alkali metal alcoholate or alkaline earth metal alcoholate, such as sodium methylate, sodium ethylate or potassium tert-butylate, or an organic nitrogen base, such as triethylamine or pyridine, and the organic base may simultaneously serve as the solvent.

Starting materials are advantageously used in roughly stoichiometric amounts, or one of the components is used in an excess of up to about 20 mol %. If the reaction is carried out in the absence of a solvent and in the presence of an organic base, the latter is advantageously present in an even larger excess.

The reaction temperature is in general from −80° to 150° C., preferably from −30° C. to the boiling point of the respective reaction mixture.

The enaminocarboxylates of the formula V are also novel; they too can be prepared in a manner known per se, for example by reacting an amide XV with a urethane XVI according to process P):

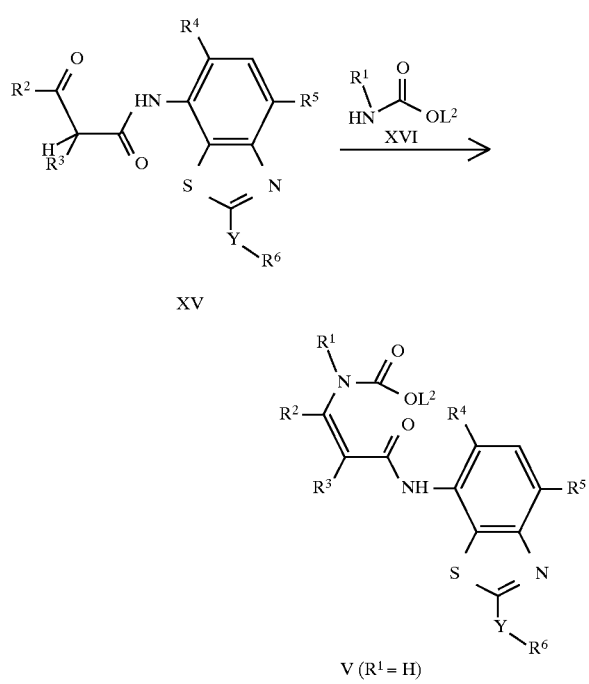

$L^2$ is low molecular weight alkyl, preferably $C_1$–$C_4$-alkyl, or phenyl.

The reaction is advantageously carried out in a substantially anhydrous solvent/diluent at atmospheric pressure, particularly preferably in the presence of an acidic catalyst.

For the preparation of enaminocarboxylates V where $R^1$ is amino, it is advisable to use compounds XVI having a protected amino group (for example as hydrazone).

Particularly suitable solvents/diluents are organic liquids capable of forming an azeotropic mixture with water, for example aromatics, such as benzene, toluene and o-, m- or p-xylene, and halogenated hydrocarbons, such as carbon tetrachloride and chlorobenzene.

Particularly suitable catalysts are strong mineral acids, such as sulfuric acid, organic acids, such as p-toluenesulfonic acid, phosphorus-containing acids, such as orthophosphoric acid and polyphosphoric acid, and acidic cation exchangers, such as Amberlyst 15 (from Fluka).

In general, a reaction temperature of from about 70° to 150° C. is sufficient; however, for rapid removal of the water of reaction formed, the reaction is advantageously carried out at the boiling point of the respective reaction mixture.

XV and XVI are usually used in roughly stoichiometric amounts; XVI is preferably used in a slight excess of up to about 20 mol %.

The amide XV can be prepared as follows: Q):

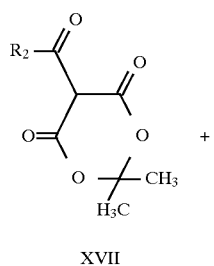

XVII

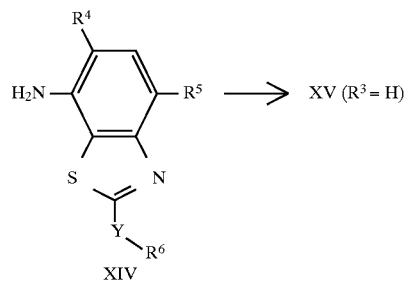

XIV

The reaction is preferably carried out in an anhydrous inert aprotic solvent, for example in a halogenated hydrocarbon, such as methylene chloride, chloroform, carbon tetrachloride or chlorobenzene, an aromatic hydrocarbon, such as benzene, toluene or o-, m- or p-xylene, or an aliphatic or cyclic ether, such as diethyl ether, dibutyl ether, 1,2-dimethoxyethane, tetrahydrofuran or dioxane.

The reaction temperature is in general from about 70° to 140° C., in particular from 100° to 120° C.

XVII and XIV are usually used in roughly stoichiometric amounts, or one of the components is used in an excess of up to about 10 mol %.
R):

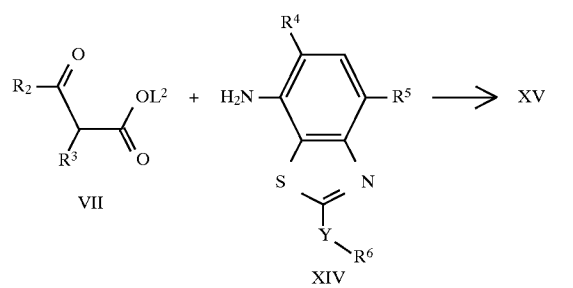

The aminolysis of VII with XIV can be carried out in the absence of a solvent (cf. for example J. Chem. Soc. Dyes Col. 42 (1926), 81); Ber. 64 (1931), 970; Org. Synth. Coll. IV (1963), 80; J. Am. Chem. Soc. 70 (1948), 2402) or in an inert anhydrous solvent/diluent, in particular in an aprotic solvent, for example an aromatic, such as toluene or one of the xylenes, or a halogenated aromatic, such as chlorobenzene.

Here, it is advisable to carry out the reaction in the presence of a basic catalyst, for example a relatively high-boiling amine (cf. for example Helv. Chim. Acta 11 (1928), 779, and U.S. Pat. No. 2,416,738) or pyridine.

The reaction temperature is preferably from about 130° to 160° C.

The starting compounds are advantageously reacted in roughly stoichiometric amounts, or a slight excess, up to about 10 mol %, of one or other of the components used. If the reaction is carried out in the presence of a basic catalyst, from 0.5 to 2 mol %, based on the amount of one of the starting materials, of the catalyst are usually sufficient.

The starting compounds stated for the individual processes are either known or are obtainable in a manner known per se or by a process similar to one of the processes described.

The isocyanates XI and the aniline derivatives XIV are novel if Y is —SO— or —SO$_2$—. Preferred among these are those compounds XI and XIV in which $R^4$, $R^5$ and/or $R^6$ have the following meanings:

$R^4$ is hydrogen, fluorine, chlorine or bromine;

$R^5$ is cyano or halogen, in particular cyano, fluorine, chlorine or bromine;

$R^6$ is $C_1$–$C_6$-haloalkyl, $C_3$–$C_6$-alkenyl, $C_3$'$C_6$-alkynyl or $C_1$–$C_6$-alkyl which may be unsubstituted or substituted by cyano, $C_1$–$C_6$-alkoxy, ($C_1$–$C_6$-alkoxy)carbonyl, ($C_1$–$C_6$-alkyl)carbonyloxy or $C_1$–$C_6$-haloalkoxy.

Particularly preferred compounds XI and XIV are those in which $R^6$ is one of the radicals from the group 6.101–6.149 (Table 3):

TABLE 3

| No. | $R^6$ |
|---|---|
| 6.101 | CH$_2$Cl |
| 6.102 | CH$_2$F |
| 6.103 | CHF$_2$ |
| 6.104 | CF$_3$ |
| 6.105 | CClF$_2$ |
| 6.106 | CCl$_2$F |
| 6.107 | CH$_2$CH$_2$Cl |
| 6.108 | CH$_2$CH$_2$F |
| 6.109 | CH$_2$CH$_2$Br |
| 6.110 | CH$_2$CH$_2$I |
| 6.111 | CH$_2$CF$_3$ |
| 6.112 | CF$_2$CF$_3$ |
| 6.113 | CH$_2$CH=CH$_2$ |
| 6.114 | CH(CH$_3$)CH=CH$_2$ |
| 6.115 | CH$_2$CH=CHCH$_3$ |
| 6.116 | CH(CH$_3$)CH=CH—CH$_3$ |
| 6.117 | CH$_2$C≡CH |
| 6.118 | CH(CH$_3$)C≡CH |
| 6.119 | CH$_3$ |
| 6.120 | CH$_2$CH$_3$ |
| 6.121 | n-C$_3$H$_7$ |
| 6.122 | i-C$_3$H$_7$ |
| 6.123 | n-C$_4$H$_9$ |
| 6.124 | i-C$_4$H$_9$ |
| 6.125 | s-C$_4$H$_9$ |
| 6.126 | t-C$_4$H$_9$ |
| 6.127 | n-C$_5$H$_{11}$ |
| 6.128 | n-C$_6$H$_{13}$ |
| 6.129 | CH$_2$CN |
| 6.130 | CH(CH$_3$)CN |
| 6.131 | CH$_2$CH$_2$CN |
| 6.132 | CH(CH$_3$)CH$_2$CN |

TABLE 3-continued

| No. | R⁶ |
|---|---|
| 6.133 | $CH_2CH_2OCH_3$ |
| 6.134 | $CH_2CH_2OCH_2CH_3$ |
| 6.135 | $CH(CH_3)CH_2OCH_3$ |
| 6.136 | $CH(CH_3)CH_2OCH_2CH_3$ |
| 6.137 | $CH_2COOCH_3$ |
| 6.138 | $CH_2COOCH_2CH_3$ |
| 6.139 | $CH_2COOCH(CH_3)_2$ |
| 6.140 | $CH(CH_3)COOCH_3$ |
| 6.141 | $CH(CH_3)COOCH_2CH_3$ |
| 6.142 | $CH(CH_3)COOCH(CH_3)_2$ |
| 6.143 | $CH_2CH_2COOCH_3$ |
| 6.144 | $CH_2CH_2COOCH_2CH_3$ |
| 6.145 | $CH(CH_2CH_3)COOCH_3$ |
| 6.146 | $CH(CH_2CH_3)COOCH_2CH_3$ |
| 6.147 | $CH_2CH_2OCOCH_3$ |
| 6.148 | $CH_2CH_2OCHF_2$ |
| 6.149 | $CH_2CH_2OCH_2CF_3$ |

The aniline derivatives XIVa (= XIV where $R^5$ is Cl and Y is —SO—), in particular the compounds XIVa.1 to XIVa.188 shown in Table 4, are very particularly preferred:

TABLE 4

| No. | R⁴ | R⁶ |
|---|---|---|
| XIVa.1 | H | $CH_3$ |
| XIVa.2 | F | $CH_3$ |
| XIVa.3 | Cl | $CH_3$ |
| XIVa.4 | Br | $CH_3$ |
| XIVa.5 | H | $CH_2CH_3$ |
| XIVa.6 | F | $CH_2CH_3$ |
| XIVa.7 | Cl | $CH_2CH_3$ |
| XIVa.8 | Br | $CH_2CH_3$ |
| XIVa.9 | H | $CH_2CH_2CH_3$ |
| XIVa.10 | F | $CH_2CH_2CH_3$ |
| XIVa.11 | Cl | $CH_2CH_2CH_3$ |
| XIVa.12 | Br | $CH_2CH_2CH_3$ |
| XIVa.13 | H | $CH(CH_3)_2$ |
| XIVa.14 | F | $CH(CH_3)_2$ |
| XIVa.15 | Cl | $CH(CH_3)_2$ |
| XIVa.16 | Br | $CH(CH_3)_2$ |
| XIVa.17 | H | $CH_2CH_2CH_2CH_3$ |
| XIVa.18 | F | $CH_2CH_2CH_2CH_3$ |
| XIVa.19 | Cl | $CH_2CH_2CH_2CH_3$ |
| XIVa.20 | Br | $CH_2CH_2CH_2CH_3$ |
| XIVa.21 | H | $CHCH(CH_3)_2$ |
| XIVa.22 | F | $CHCH(CH_3)_2$ |
| XIVa.23 | Cl | $CHCH(CH_3)_2$ |
| XIVa.24 | Br | $CHCH(CH_3)_2$ |
| XIVa.25 | H | $C(CH_3)_3$ |
| XIVa.26 | F | $C(CH_3)_3$ |
| XIVa.27 | Cl | $C(CH_3)_3$ |
| XIVa.28 | Br | $C(CH_3)_3$ |
| XIVa.29 | H | $CH(CH_3)CH_2CH_3$ |
| XIVa.30 | F | $CH(CH_3)CH_2CH_3$ |
| XIVa.31 | Cl | $CH(CH_3)CH_2CH_3$ |
| XIVa.32 | Br | $CH(CH_3)CH_2CH_3$ |
| XIVa.33 | H | $CH_2CH=CH_2$ |
| XIVa.34 | F | $CH_2CH=CH_2$ |
| XIVa.35 | Cl | $CH_2CH=CH_2$ |
| XIVa.36 | Br | $CH_2CH=CH_2$ |
| XIVa.37 | H | $CH(CH_3)CH=CH_2$ |

TABLE 4-continued

| No. | R⁴ | R⁶ |
|---|---|---|
| XIVa.38 | F | $CH(CH_3)CH=CH_2$ |
| XIVa.39 | Cl | $CH(CH_3)CH=CH_2$ |
| XIVa.40 | Br | $CH(CH_3)CH=CH_2$ |
| XIVa.41 | H | $CH_2C\equiv CH$ |
| XIVa.42 | F | $CH_2C\equiv CH$ |
| XIVa.43 | Cl | $CH_2C\equiv CH$ |
| XIVa.44 | Br | $CH_2C\equiv CH$ |
| XIVa.45 | H | $CH(CH_3)C\equiv CH$ |
| XIVa.46 | F | $CH(CH_3)C\equiv CH$ |
| XIVa.47 | Cl | $CH(CH_3)C\equiv CH$ |
| XIVa.48 | Br | $CH(CH_3)C\equiv CH$ |
| XIVa.49 | H | $CH_2C\equiv C-CH_3$ |
| XIVa.50 | F | $CH_2C\equiv C-CH_3$ |
| XIVa.51 | Cl | $CH_2C\equiv C-CH_3$ |
| XIVa.52 | Br | $CH_2C\equiv C-CH_3$ |
| XIVa.53 | H | $CH_2Cl$ |
| XIVa.54 | F | $CH_2Cl$ |
| XIVa.55 | Cl | $CH_2Cl$ |
| XIVa.56 | Br | $CH_2Cl$ |
| XIVa.57 | H | $CH_2F$ |
| XIVa.58 | F | $CH_2F$ |
| XIVa.59 | Cl | $CH_2F$ |
| XIVa.60 | Br | $CH_2F$ |
| XIVa.61 | H | $CHF_2$ |
| XIVa.62 | F | $CHF_2$ |
| XIVa.63 | Cl | $CHF_2$ |
| XIVa.64 | Br | $CHF_2$ |
| XIVa.65 | H | $CF_3$ |
| XIVa.66 | F | $CF_3$ |
| XIVa.67 | Cl | $CF_3$ |
| XIVa.68 | Br | $CF_3$ |
| XIVa.69 | H | $CClF_2$ |
| XIVa.70 | F | $CClF_2$ |
| XIVa.71 | Cl | $CClF_2$ |
| XIVa.72 | Br | $CClF_2$ |
| XIVa.73 | H | $CCl_2F$ |
| XIVa.74 | F | $CCl_2F$ |
| XIVa.75 | Cl | $CCl_2F$ |
| XIVa.76 | Br | $CCl_2F$ |
| XIVa.77 | H | $CH_2CH_2Cl$ |
| XIVa.78 | F | $CH_2CH_2Cl$ |
| XIVa.79 | H | $CH_2CH_2Cl$ |
| XIVa.80 | H | $CH_2CH_2Cl$ |
| XIVa.81 | H | $CH_2CH_2F$ |
| XIVa.82 | F | $CH_2CH_2F$ |
| XIVa.83 | Cl | $CH_2CH_2F$ |
| XIVa.84 | Br | $CH_2CH_2F$ |
| XIVa.85 | H | $CH_2CF_3$ |
| XIVa.86 | F | $CH_2CF_3$ |
| XIVa.87 | Cl | $CH_2CF_3$ |
| XIVa.88 | Br | $CH_2CF_3$ |
| XIVa.89 | H | $CF_2CF_3$ |
| XIVa.90 | F | $CF_2CF_3$ |
| XIVa.91 | Cl | $CF_2CF_3$ |
| XIVa.92 | Br | $CF_2CF_3$ |
| XIVa.93 | H | $CH_2CN$ |
| XIVa.94 | F | $CH_2CN$ |
| XIVa.95 | Cl | $CH_2CN$ |

TABLE 4-continued

XIVa structure: H$_2$N-phenyl-Cl with R$^4$ substituent, and S-C(=N)-SO-R$^6$ fused group

| No. | R$^4$ | R$^6$ |
|---|---|---|
| XIVa.96 | Br | CH$_2$CN |
| XIVa.97 | H | CH(CH$_3$)CN |
| XIVa.98 | F | CH(CH$_3$)CN |
| XIVa.99 | Cl | CH(CH$_3$)CN |
| XIVa.100 | Br | CH(CH$_3$)CN |
| XIVa.101 | H | CH$_2$CH$_2$CN |
| XIVa.102 | F | CH$_2$CH$_2$CN |
| XIVa.103 | Cl | CH$_2$CH$_2$CN |
| XIVa.104 | Br | CH$_2$CH$_2$CN |
| XIVa.105 | H | CH(CH$_3$)CH$_2$CN |
| XIVa.106 | F | CH(CH$_3$)CH$_2$CN |
| XIVa.107 | Cl | CH(CH$_3$)CH$_2$CN |
| XIVa.108 | Br | CH(CH$_3$)CH$_2$CN |
| XIVa.109 | H | CH$_2$CH$_2$OCH$_3$ |
| XIVa.110 | F | CH$_2$CH$_2$OCH$_3$ |
| XIVa.111 | Cl | CH$_2$CH$_2$OCH$_3$ |
| XIVa.112 | Br | CH$_2$CH$_2$OCH$_3$ |
| XIVa.113 | H | CH$_2$CH$_2$OCH$_2$CH$_3$ |
| XIVa.114 | F | CH$_2$CH$_2$OCH$_2$CH$_3$ |
| XIVa.115 | Cl | CH$_2$CH$_2$OCH$_2$CH$_3$ |
| XIVa.116 | Br | CH$_2$CH$_2$OCH$_2$CH$_3$ |
| XIVa.117 | H | CH(CH$_3$)CH$_2$OCH$_3$ |
| XIVa.118 | F | CH(CH$_3$)CH$_2$OCH$_3$ |
| XIVa.119 | Cl | CH(CH$_3$)CH$_2$OCH$_3$ |
| XIVa.120 | Br | CH(CH$_3$)CH$_2$OCH$_3$ |
| XIVa.121 | H | CH(CH$_3$)CH$_2$OCH$_2$CH$_3$ |
| XIVa.122 | F | CH(CH$_3$)CH$_2$OCH$_2$CH$_3$ |
| XIVa.123 | Cl | CH(CH$_3$)CH$_2$OCH$_2$CH$_3$ |
| XIVa.124 | Br | CH(CH$_3$)CH$_2$OCH$_2$CH$_3$ |
| XIVa.125 | H | CH$_2$COOCH$_3$ |
| XIVa.126 | F | CH$_2$COOCH$_3$ |
| XIVa.127 | Cl | CH$_2$COOCH$_3$ |
| XIVa.128 | Br | CH$_2$COOCH$_3$ |
| XIVa.129 | H | CH$_2$COOCH$_2$CH$_3$ |
| XIVa.130 | F | CH$_2$COOCH$_2$CH$_3$ |
| XIVa.131 | Cl | CH$_2$COOCH$_2$CH$_3$ |
| XIVa.132 | Br | CH$_2$COOCH$_2$CH$_3$ |
| XIVa.133 | H | CH$_2$COOCH(CH$_3$)$_2$ |
| XIVa.134 | F | CH$_2$COOCH(CH$_3$)$_2$ |
| XIVa.135 | Cl | CH$_2$COOCH(CH$_3$)$_2$ |
| XIVa.136 | Br | CH$_2$COOCH(CH$_3$)$_2$ |
| XIVa.137 | H | CH(CH$_3$)COOCH$_3$ |
| XIVa.138 | F | CH(CH$_3$)COOCH$_3$ |
| XIVa.139 | Cl | CH(CH$_3$)COOCH$_3$ |
| XIVa.140 | Br | CH(CH$_3$)COOCH$_3$ |
| XIVa.141 | H | CH(CH$_3$)COOCH$_2$CH$_3$ |
| XIVa.142 | F | CH(CH$_3$)COOCH$_2$CH$_3$ |
| XIVa.143 | Cl | CH(CH$_3$)COOCH$_2$CH$_3$ |
| XIVa.144 | Br | CH(CH$_3$)COOCH$_2$CH$_3$ |
| XIVa.145 | H | CH$_2$CH$_2$COOCH$_3$ |
| XIVa.146 | F | CH$_2$CH$_2$COOCH$_3$ |
| XIVa.147 | Cl | CH$_2$CH$_2$COOCH$_3$ |
| XIVa.148 | Br | CH$_2$CH$_2$COOCH$_3$ |
| XIVa.149 | H | CH$_2$CH$_2$COOCH$_2$CH$_3$ |
| XIVa.150 | F | CH$_2$CH$_2$COOCH$_2$CH$_3$ |
| XIVa.151 | Cl | CH$_2$CH$_2$COOCH$_2$CH$_3$ |
| XIVa.152 | H | CH$_2$CH$_2$COOCH$_2$CH$_3$ |
| XIVa.153 | H | CH(CH$_2$CH$_3$)COOCH$_3$ |
| XIVa.154 | F | CH(CH$_2$CH$_3$)COOCH$_3$ |
| XIVa.155 | Cl | CH(CH$_2$CH$_3$)COOCH$_3$ |
| XIVa.156 | Br | CH(CH$_2$CH$_3$)COOCH$_3$ |
| XIVa.157 | H | CH(CH$_2$CH$_3$)COOCH$_2$CH$_3$ |
| XIVa.158 | F | CH(CH$_2$CH$_3$)COOCH$_2$CH$_3$ |
| XIVa.159 | Cl | CH(CH$_2$CH$_3$)COOCH$_2$CH$_3$ |
| XIVa.160 | Br | CH(CH$_2$CH$_3$)COOCH$_2$CH$_3$ |
| XIVa.161 | H | CH[CH(CH$_3$)$_2$]COOCH$_3$ |
| XIVa.162 | F | CH[CH(CH$_3$)$_2$]COOCH$_3$ |
| XIVa.163 | Cl | CH[CH(CH$_3$)$_2$]COOCH$_3$ |
| XIVa.164 | Br | CH[CH(CH$_3$)$_2$]COOCH$_3$ |
| XIVa.165 | H | CH$_2$CH$_2$OCOCH$_3$ |
| XIVa.166 | F | CH$_2$CH$_2$OCOCH$_3$ |
| XIVa.167 | Cl | CH$_2$CH$_2$OCOCH$_3$ |
| XIVa.168 | Br | CH$_2$CH$_2$OCOCH$_3$ |
| XIVa.169 | H | CH$_2$CH$_2$OCOCH$_2$CH$_3$ |
| XIVa.170 | F | CH$_2$CH$_2$OCOCH$_2$CH$_3$ |
| XIVa.171 | Cl | CH$_2$CH$_2$OCOCH$_2$CH$_3$ |
| XIVa.172 | Br | CH$_2$CH$_2$OCOCH$_2$CH$_3$ |
| XIVa.173 | H | CH(CH$_3$)CH$_2$OCOCH$_3$ |
| XIVa.174 | F | CH(CH$_3$)CH$_2$OCOCH$_3$ |
| XIVa.175 | Cl | CH(CH$_3$)CH$_2$OCOCH$_3$ |
| XIVa.176 | Br | CH(CH$_3$)CH$_2$OCOCH$_3$ |
| XIVa.177 | H | CH$_2$CH(CH$_3$)OCOCH$_3$ |
| XIVa.178 | F | CH$_2$CH(CH$_3$)OCOCH$_3$ |
| XIVa.179 | Cl | CH$_2$CH(CH$_3$)OCOCH$_3$ |
| XIVa.180 | Br | CH$_2$CH(CH$_3$)OCOCH$_3$ |
| XIVa.181 | H | CH$_2$CH$_2$OCHF$_3$ |
| XIVa.182 | F | CH$_2$CH$_2$OCHF$_3$ |
| XIVa.183 | Cl | CH$_2$CH$_2$OCHF$_3$ |
| XIVa.184 | Br | CH$_2$CH$_2$OCHF$_3$ |
| XIVa.185 | H | CH$_2$CH$_2$OCH$_2$CF$_3$ |
| XIVa.186 | F | CH$_2$CH$_2$OCH$_2$CF$_3$ |
| XIVa.187 | Cl | CH$_2$CH$_2$OCH$_2$CF$_3$ |
| XIVa.188 | Br | CH$_2$CH$_2$OCH$_2$CF$_3$ |

Furthermore, the isocyanates XIa to XIh and the aniline derivatives XIVb to XIVh are very particularly preferred, in particular:

the compounds XIa.1–XIa.188 in which Y and R$^4$ to R$^6$ have the same meanings as in the corresponding compounds XIVa.1–XIVa.188:

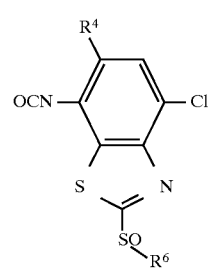

XIa the compounds XIVb.1–XIVb.188 which differ from the compounds XIVa.1–XIVa.188 only in that Y is —SO$_2$—:

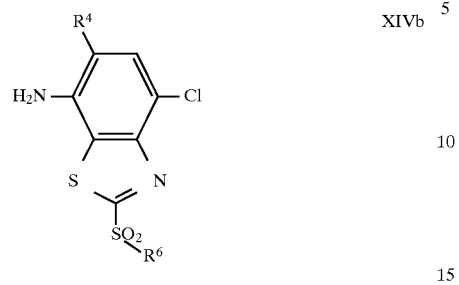

XIVb the compounds XIb.1–XIb.188 in which Y and R$^4$ to R$^6$ have the same meanings as in the corresponding compounds XIVb.1–XIVb.188:

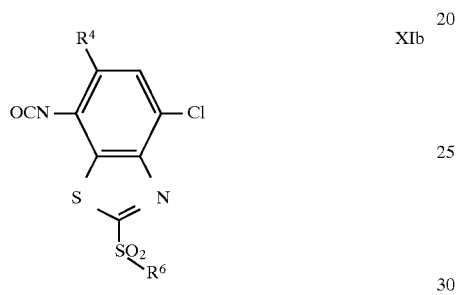

XIb the compounds XIVc.1–XIVc.188 which differ from the compounds XIVa.1–XIVa.188 only in that R$^5$ is fluorine:

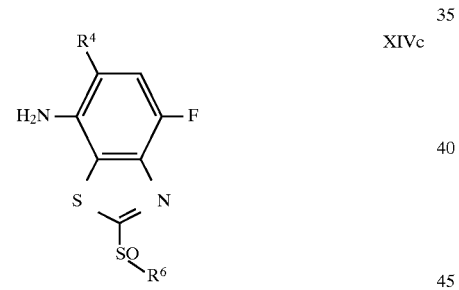

XIVc the compounds XIc.1–XIc.188 in which Y and R$^4$ to R$^6$ have the same meanings as in the corresponding compounds XIVc.1–XIVc.188:

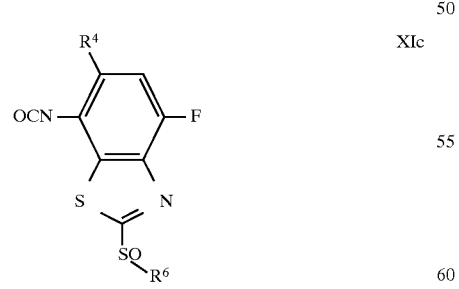

XIc the compounds XIVd.1–XIVd.188 which differ from the compounds XIVa.1–XIVa.188 only in that R$^5$ is fluorine and Y is —SO$_2$—:

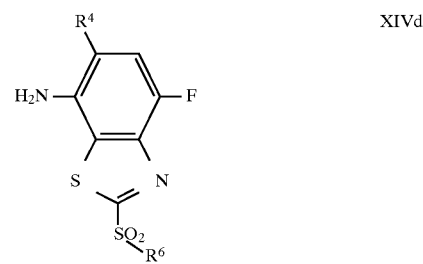

XIVd the compounds XId.1–XId.188 in which Y and R$^4$ to R$^6$ have the same meanings as in the corresponding compounds XIVd.1–XIVd.188:

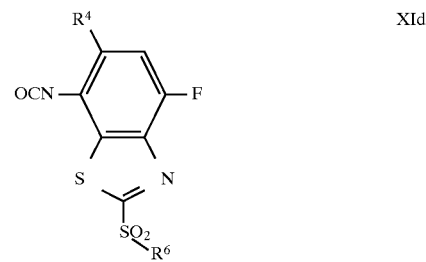

XId the compounds XIVe.1–XIVe.188 which differ from the compounds XIVa.1–XIVa.188 only in that R$^5$ is bromine:

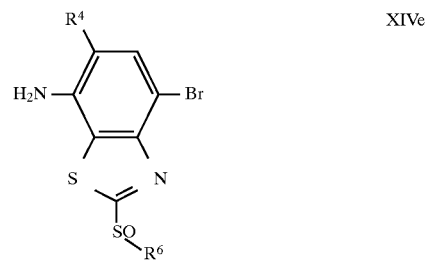

XIVe the compounds XIe.1–XIe.188 in which Y and R$^4$ to R$^6$ have the same meanings as in the corresponding compounds XIVe.1–XIVe.188:

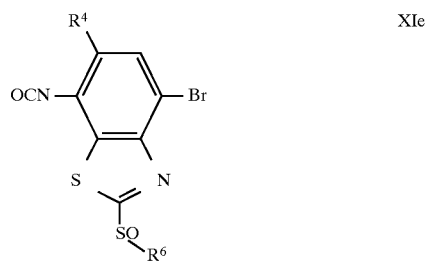

XIe the compounds XIVf.1–XIVf.188 which differ from the compounds XIVa.1–XIVa.188 only in that $R^5$ is bromine and Y is —$SO_2$—:

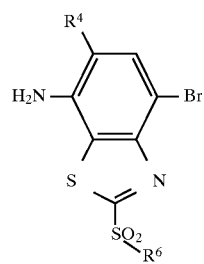

XIVf the compounds XIf.1–XIf.188 in which Y and $R^4$ to $R^6$ have the same meanings as in the corresponding compounds XIVf.1–XIVf.188:

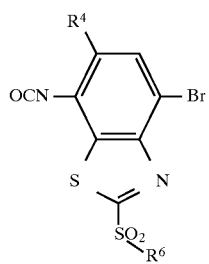

XIf the compounds XIVg.1–XIVg.188 which differ from the compounds XIVa.1–XIVa.188 only in that $R^5$ is cyano:

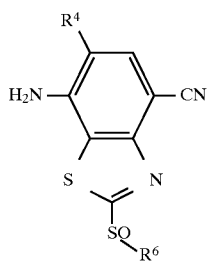

XIVg the compounds XIg.1–XIg.188 in which Y and $R^4$ to $R^6$ have the same meanings as in the corresponding compounds XIVg.1–XIVg.188:

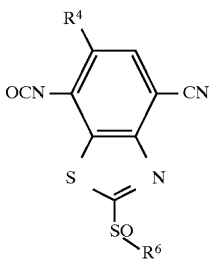

XIg the compounds XIVh.1–XIVh.188, which differ from the compounds XIVa.1–XIVa.188 only in that $R^5$ is cyano and Y is —$SO_2$—:

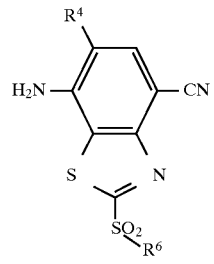

XIVh the compounds XIh.1–XIh.188 in which Y and $R^4$ to $R^6$ have the same meanings as in the corresponding compounds XIVh.1–XIVh.188:

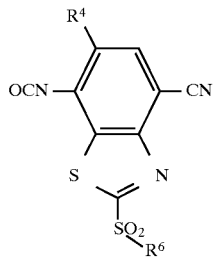

XIh

The isocyanates XI are obtainable, for example, from the aniline derivatives XIV according to process S):

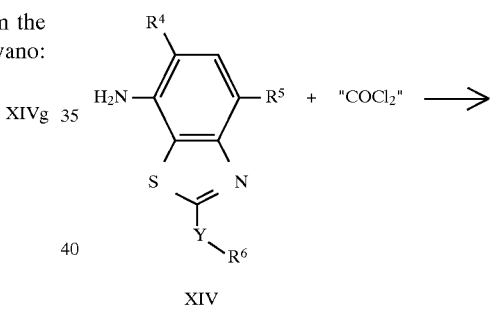

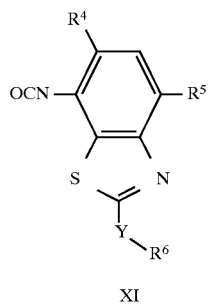

XI

The process can be carried out in an inert, essentially anhydrous solvent or diluent or in the absence of a solvent, the aniline derivatives XIV preferably being reacted with phosgene, with a phosgene equivalent, such as diphosgene, triphosgene or carbonyldiimidazole, or with trichloromethyl chloroformate.

Particularly suitable solvents or diluents are aprotic, organic solvents, for example aromatics, such as toluene and o-, m- and p-xylene, halogenated hydrocarbons, such as methylene chloride, chloroform, 1,2-dichloroethane and chlorobenzene, aliphatic and cyclic ethers, such as 1,2-dimethoxyethane, tetrahydrofuran and dioxane, and esters, such as ethyl acetate, and mixtures of these solvents.

The starting materials are advantageously used in roughly stoichiometric amounts, or one of the components is used in an excess of up to about 200 mol %.

Depending on the aniline derivative XIV used, it may be advantageous to add a base, such as triethylamine, for example in from 0.5 times to twice the molar amount, based on the amount of XIV.

The reaction temperature is in general from −20° C. to the reflux temperature of the solvent or reaction mixture.

The aniline derivatives XIV are in turn obtainable in a manner known per se (cf. for example Houben-Weyl, Methoden der organischen Chemie, Georg Thieme Verlag, vol. XI/1, 4th edition 1957, page 431 et seq.), by reduction of the corresponding nitroderivatives XVIII:

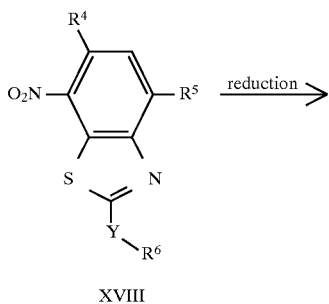

XVIII

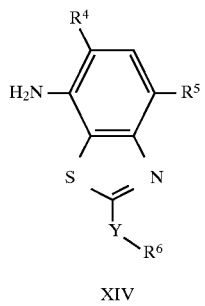

XIV

Particularly suitable reducing agents are elemental metals, such as iron, tin and zinc, hydrogen in the presence of suitable catalysts, such as palladium or platinum on carbon or Raney nickel, or complex hydrides, such as LiAlH$_4$ and NaBH$_4$, in the presence or absence of catalysts.

Depending on the reducing agent, suitable solvents are usually carboxylic acids, such as acetic acid and propionic acid, alcohols, such as methanol and ethanol, ethers, such as diethyl ether, methyl tert-butyl ether, tetrahydrofuran and dioxane, aromatics, such as benzene and toluene, and mixtures of such solvents.

The reactions can be carried out at from −100° C. to the boiling point of the respective reaction mixture.

The starting compounds are usually used in roughly stoichiometric amounts; in individual cases, however, an excess of up to about 10 mol % of one or other component may also be advantageous.

The compounds XI and XIV, too, may contain one or more centers of chirality and are then usually obtained as enantiomer or diastereomer mixtures. The mixtures can, if desired, be separated into the substantially pure isomers by the conventional methods, for example by means of crystallization or chromatography over an optically active adsorbate. Pure optically active isomers can also be prepared, for example, from corresponding optically active starting materials.

Unless stated otherwise, all processes described above are advantageously carried out at atmospheric pressure or under the autogenous pressure of the respective reaction mixture.

The reaction mixtures are worked up, as a rule, by methods known per se, for example by dilution of the reaction mixture with water and subsequent isolation of the desired product by means of filtration, crystallization or solvent extraction, or by removal of the solvent, partition of the residue in a mixture of water and a suitable organic solvent and working up of the organic phase to obtain the product.

In general, the substituted benzothiazoles I can be prepared by one of the abovementioned synthesis methods. For economic or process engineering reasons, however, it may be more advantageous to prepare some compounds I from similar substituted benzothiazoles I, which however differ in particular in the meaning of R$^6$.

The compounds I and their agriculturally useful salts—both as isomer mixtures and in the form of pure isomers—are suitable as herbicides. The herbicides containing them provide very effective control of plant growth on uncultivated areas, particularly at high application rates. They act against broad-leaved weeds and grass weeds in crops such as wheat, rice, corn, soybean and cotton, without significantly damaging the crops. This effect occurs in particular at low application rates.

Depending on the respective application method, the compounds I or the herbicides containing them can also be used in a further number of crops for eliminating undesirable plants. For example, the following crops are suitable: *Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec.*, Manihot esculenta, Medicago sativa, Musa* spec.*, Nicotiana tabacum* (*N.rustica*), *Olea europaea, Oryza sativa, Phaseolus lunatus, Phaseolus vulgaris, Picea abies, Pinus* spec.*, Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays.*

In addition, the compounds I can also be used in crops which are tolerant to the action of herbicides as a result of breeding, including genetic engineering methods.

Substituted benzothiazoles I are also suitable for desiccating and/or defoliating plants.

As desiccants, they are particularly suitable for drying out the above-ground parts of crops, such as potatoes, rape, sunflower and soybean. This permits complete mechanical harvesting of these important crops.

Also of commercial interest is the facilitation of harvesting, which is permitted by the concentrated dropping or reduction in the adhesion to the tree in the case of citrus fruits, olives or other species and varieties of pomes, drupes and indehiscent fruit. The same mechanism, ie. promotion of the formation of abscission tissue between fruit part or leaf part and shoot part of the plants is also important for readily controllable defoliation of crops, in particular cotton.

Furthermore, shortening of the time interval in which the individual cotton plants ripen leads to higher fiber quality after the harvest.

The compounds I or the herbicides containing them can be applied, for example, in the form of directly sprayable aqueous solutions, powders, suspensions, including concentrated aqueous, oily or other suspensions or dispersions, emulsions, oil dispersions, pastes, dusting agents, broadcasting agents or granules, by spraying, nebulizing, dusting, broadcasting or pouring. The application forms depend on the intended uses; they should in any case ensure a very fine distribution of the novel active ingredients.

Suitable inert assistants are essentially mineral oil fractions having a medium to high boiling point, such as kerosene and diesel oil, and coal tar oils and oils of vegetable or animal origin, aliphatic, cyclic and aromatic hydrocarbons, for example paraffins, tetrahydronaphthalene, alkylated naphthalenes and derivatives thereof, alkylated benzenes and derivatives thereof, alcohols, such as methanol, ethanol, propanol, butanol and cyclohexanol, ketones, such as cyclohexanone, strongly polar solvents, for example amines, such as N-methylpyrrolidone, and water.

Aqueous application forms can be prepared from emulsion concentrates, suspensions, pastes, wettable powders or water-dispersible granules by adding water. For the preparation of emulsions, pastes or oil dispersions, the substances, as such or dissolved in an oil or solvent, can be homogenized in water by means of wetting agents, adherents, dispersants or emulsifiers. However, it is also possible to prepare concentrates which consist of active ingredient, wetting agents, adherents, dispersants or emulsifiers and possibly solvents or oil and which are suitable for dilution with water.

Suitable surfactants (adjuvants) are alkali metal, alkaline earth metal and ammonium salts of aromatic sulfonic acids, for example lignin-, phenol-, naphthalene- and dibutylnaphthalenesulfonic acid, and of fatty acids, alkylsulfonates and alkylarylsulfonates, alkylsulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of naphthalenesulfonic acids with phenol and formaldehyde, polyoxyethylene octylphenol ether, ethoxylated isooctyl-, octyl- or nonylphenol, alkylphenyl polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxy propylene alkyl ethers, lauryl alcohol polyglycol ether acetate, sorbitol esters, ligninsulfite waste liquors or methylcellulose.

Powders, broadcasting agents and dusting agents can be prepared by mixing or milling the active ingredients together with a solid carrier.

Granules, for example coated, impregnated and homogeneous granules, can be prepared by binding the active ingredients to solid carriers. Solid carriers are mineral earths, such as silica, silica gels, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate and ureas, and vegetable products, such as grain flour, bark meal, wood meal and nutshell meal, cellulosic powders and other solid carriers.

The concentrations of the active ingredients I in the ready-to-use formulations can be varied within wide ranges. The formulations generally contain from 0.001 to 98, preferably from 0.01 to 95, % by weight, of at least one active ingredient. The active ingredients are used in a purity of from 90 to 100%, preferably from 95 to 100% (according to NMR spectrum).

The following formulation examples illustrate the preparation of such formulations:

I. 20 parts by weight of compound No. I.2 are dissolved in a mixture which consists of 80 parts by weight of alkylated benzene, 10 parts by weight of the adduct of from 8 to 10 mol of ethylene oxide with 1 mol of N-monoethanololeamide, 5 parts by weight of calcium salt of dodecylbenzenesulfonic acid and 5 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

II. 20 parts by weight of compound No. I.3 are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

III. 20 parts by weight of active ingredient No. I.5 are dissolved in a mixture which consists of 25 parts by weight of cyclohexanone, 65 parts by weight of a mineral oil fraction boiling within the range from 210° to 280° C. and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

IV. 20 parts by weight of active ingredient No. I.7 are thoroughly mixed with 3 parts by weight of the sodium salt of diisobutylnaphthalene-a-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

V. 3 parts by weight of active ingredient No. I.33 are mixed with 97 parts by weight of finely divided kaolin. A dusting agent which contains 3% by weight of the active ingredient is obtained in this manner.

VI. 20 parts by weight of active ingredient No. I.11 are thoroughly mixed with 2 parts by weight of the calcium salt of dodecylbenzenesulfonic acid, 8 parts by weight of a fatty alcohol polyglycol ether, 2 parts by weight of sodium salt of a phenol/urea/formaldehyde condensate and 68 parts by weight of a paraffinic mineral oil. A stable oily dispersion is obtained.

VII. 1 part by weight of active ingredient No. I.9 is dissolved in a mixture which consists of 70 parts by weight of cyclohexanone, 20 parts by weight of ethoxylated isooctylphenol and 10 parts by weight of ethoxylated castor oil. A stable emulsion concentrate is obtained.

VIII. 1 part by weight of active ingredient No. I.14 is dissolved in a mixture which consists of 80 parts by weight of cyclohexanone and 20 parts by weight of Wettol® EM 31 (= nonionic emulsifier based on ethoxylated castor oil; BASF AG). A stable emulsion concentrate is obtained.

The active ingredients I or the herbicides can be applied by the preemergence or postemergence method. If the active ingredients are less tolerated by certain crops, it is possible to use application methods in which the herbicides are sprayed with the aid of the sprayers so that the leaves of the sensitive crops are as far as possible not affected, whereas the active ingredients reach the leaves of undesirable plants growing underneath or the uncovered soil surface (post-directed, lay-by).

The application rates of active ingredient I are from 0.001 to 3.0, preferably from 0.01 to 1.0, kg/ha of active ingredient (a.i.), depending on the aim of control, the season, the target plants and the stage of growth.

In order to broaden the action spectrum and to achieve synergistic effects, the substituted benzothiazoles I can be mixed with a large number of substances of other groups of herbicidal or growth-regulating active ingredients and can be applied together with these. Suitable components of the mixture are, for example, 1,2,4-thiadiazoles, 1,3,4-thiadiazoles, amides, aminophosphoric acid and its derivatives, aminotriazoles, anilides, aryloxy-/hetaryloxyalkanoic acids and their derivatives, benzoic acid and its derivatives, benzothiadiazinones, 2-(hetaroyl/aroyl)-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarbonxylic acid and its derivatives, pyrimidyl ethers, sulfonamides, sulfonylureas, triazines, triazinones, triazolinones, triazolecarboxamides and uracils.

It may also be useful to apply the compounds I, alone or in combination with other herbicides, also as a mixture with further crop protection agents, for example with pesticides or agents for controlling phytopathogenic fungi or bacteria. Also of interest is the miscibility with mineral salt solutions which are used for eliminating nutrient and trace element deficiencies. Nonphytotoxic oils and oil concentrates may also be added.

PREPARATION EXAMPLES

EXAMPLE 1

3-[2,4-Dichloro-6-fluorobenzothiazol-7-yl]-6-trifluoromethyl-2,4(1H,3H)-pyrimidinedione (compound I.4)

1.6 g of sodium hydride (97% strength) in 200 ml of absolute dimethylformamide were initially taken. 11.0 g of ethyl 3-amino-4,4,4-trifluorobut-2-enecarboxylate were then added dropwise at from 0° to 5° C. Stirring was carried out for one hour at this temperature, after which the mixture was cooled to −30° C. and 16.2 g of 2,4-dichloro-6-fluoro-7-isocyanatobenzothiazole in 50 ml of absolute tetrahydrofuran were then added dropwise. The mixture was stirred for one hour at this temperature and then slowly warmed up to room temperature. Thereafter, ice water was added and the pH was brought to 3–4 with dilute hydrochloric acid, after which the product was extracted with ethyl acetate. The ester solution was dried and then evaporated down.

$^1$H-NMR (250 MHz; in $d^6$-dimethyl sulfoxide): δ [ppm] =6.43 (s,1H), 8.06 (d,1H).

EXAMPLE 2

3-[4-Chloro-6-fluoro-2-propoxybenzothiazol-7-yl]-6-trifluoromethyl-2,4(1H,3H)-pyrimidinedione (compound I.8)

108 ml of absolute n-propanol were added dropwise at room temperature to 1.1 g of sodium hydride (97% strength) in 40 ml of absolute tetrahydrofuran. Stirring was carried out for 30 minutes, after which 7.0 g of 3-[2,4-dichloro-6-fluorobenzothiazol-7-yl]-6-trifluoromethyl-2,4(1H,3H)-pyrimidinedione (compound I.4) were slowly added. Stirring was carried out for 12 hours, after which the solvent was distilled off at reduced pressure and the residue was then taken up in water. 10% strength hydrochloric acid was added to the aqueous phase until the resulting pH was from 3 to 4. The precipitate formed was separated off, washed with water and then dried. Yield: 5.2 g.

$^1$H-NMR (250 MHz; in $d^6$-dimethyl sulfoxide): δ [ppm] =0.95 (t,3H), 1.72 (sex,2H), 4.53 (t,2H), 6.46 (s,1H), 7.82 (d,1H).

EXAMPLE 3

3-[4-Chloro-6-fluoro-2-propoxybenzothiazol-7-yl]-1-methyl-6-trifluoromethyl-2,4(1H, 3H)-pyrimidinedione (compound I.9)

1.7 g of methyl iodide were added dropwise at about 20° C. to a mixture of 200 ml of absolute ethyl methyl ketone, 1.7 g of potassium carbonate and 5.0 g of 3-[4-chloro-6-fluoro-2-propoxybenzothiazol-7-yl]-6-trifluoromethyl-2,4(1H,3H)-pyrimidinedione (compound I.8). Stirring was carried out for 12 hours at room temperature, after which the insoluble components were filtered off. The clear solution obtained was evaporated down. The residue was then taken up in water, after which the solution was neutralized with dilute hydrochloric acid. The product was then extracted with ethyl acetate. The ester phase was finally dried over sodium sulfate and then evaporated down. The purification of the crude product thus obtained was carried out by chromatography over silica gel (eluent: 9:1 cyclohexane/methyl tert-butyl ether). Yield: 1.0 g.

$^1$H-NMR (250 MHz; in $CDCl_3$): δ [ppm]=1.04 (t,3H), 1.88 (sex,2H), 3.58 (s,3H), 4.58 (t,2H), 6.39 (s,1H), 7.32 (d,1H).

EXAMPLE 4

3-(4-Chloro-6-fluoro-2-methylbenzothiazol-7-yl)-6-trifluoromethyl-2,4(1H,3H)-pyrimidinedione (compound I.15)

0.5 g (20 mmol) of sodium hydride was suspended in 50 ml of dimethylformamide, and 2.7 g (15 mmol) of methyl 3-amino-4,4,4-trifluorobut-2-enoate were added while cooling with ice. After 1 hour, the mixture was cooled to −30°

C. and the isocyanate from preliminary stage 4.4, dissolved in 20 ml of tetrahydrofuran, was added to the reaction mixture. Stirring was then carried out for 16 hours at about 20° C. Thereafter, ice water was added to the reaction mixture, after which it was acidified with dilute hydrochloric acid. The desired product was extracted with ethyl acetate, after which the organic phase was dried over magnesium sulfate and was finally evaporated down. Purification of the crude product was effected by means of column chromatography over silica gel (eluent: 9:1 cyclohexane/methyl tert-butyl ether).

Yield: 1 g.

$^1$H-NMR (250 MHz; in CDCl$_3$): δ [ppm]=2.85 (s,3H), 6.26 (s,1H), 7.45 (d,1H).

Preliminary stage 4.1

4-Chloro-6-fluoro-2-methylbenzothiazole 67 ml of a solution of methyl magnesium chloride in tetrahydrofuran (3M; 0.2 mol) were added dropwise to a solution of 22 g (0.1 mol) of 2,4-dichloro-6-fluorobenzothiazole and 3.3 g (5 mmol) of dichlorobis(triphenylphosphine)nickel in 100 ml of diethyl ether. After stirring had been carried out for 2 hours, the mixture was poured onto saturated aqueous ammonium chloride solution. The desired product was extracted with diethyl ether, after which the combined organic phases were washed with water, dried over magnesium sulfate and finally evaporated down. 10 g of the desired product were obtained by crystallization from petroleum ether.

$^1$H-NMR (250 MHz; in CDCl$_3$): δ [ppm]=2.85 (s,3H), 7.24 (dd,1H), 7.41 (dd,1H).

Preliminary stage 4.2

4-Chloro-6-fluoro-2-methyl-7-nitrobenzothiazole

A solution of 7 ml of concentrated nitric acid in 6 ml of concentrated sulfuric acid was added to a solution of 10 g (50 mmol) of 4-chloro-6-fluoro-2-methylbenzothiazole in 35 ml of concentrated sulfuric acid. Stirring was carried out for 10 minutes, after which the mixture was poured into ice water. Thereafter, the suspended desired product was separated off and, for purification, was dissolved in 100 ml of 3:1 cyclohexane/ethyl acetate. After filtration over a bed of silica gel, 8 g of desired product was obtained from the remaining solution; mp.: 130° to 132° C.

Preliminary stage 4.3

7-Amino-4-chloro-6-fluoro-2-methylbenzothiazole 6 g of iron powder were added to a suspension of 8 g (32 mmol) of 4-chloro-6-fluoro-2-methyl-7-nitrobenzothiazole in 100 ml of water and 9 ml of concentrated hydrochloric acid, which suspension had been heated to 80° C., after which the mixture was refluxed for 3 hours. 200 ml of ethyl acetate were then added to the reaction mixture. The solid was filtered off. The remaining organic phase was washed with water, dried over magnesium sulfate and finally evaporated down. Yield: 4.5 g.

$^1$H-NMR (250 MHz; in CDCl$_3$): δ [ppm]=2.85 (s,3H), 3.93 (s,2H), 7.22 (d,1H).

Preliminary stage 4.4

4-Chloro-6-fluoro-7-isocyanato-2-methylbenzothiazole

A solution of 3.2 g (15 mmol) of 7-amino-4-chloro-6-fluoro-2-methylbenzothiazole and 15 g (76 mmol) of diphosgene in 150 ml of toluene was refluxed for 6 hours. The crude product obtained after evaporation was converted directly into active ingredient I.15.

EXAMPLE 5

3-(4-Chloro-6-fluoro-2-(methylthio)benzothiazol-7-yl)-6-trifluoromethyl-2,4(1H, 3H)-pyrimidinedione (compound I.10)

First, 4-chloro-6-fluoro-7-isocyanato-2-(methylthio)benzothiazole was prepared by refluxing a solution of 7 g (28 mmol) of 7-amino-4-chloro-6-fluoro-2-(methylthio)benzothiazole and 55 g (0.28 mol) of diphosgene (200 ml of toluene for 7 hours, then adding 20 g (0.1 mol) of phosgene, refluxing for a further 8 hours and finally evaporating down.

2.7 g (15 mmol) of ethyl 3-amino-4,4,4-trifluorobut-2-enoate were then added to a suspension of 0.7 g (30 mmol) of sodium hydride in 50 ml of dimethylformamide while cooling with ice. Stirring was carried out for one hour, after which the mixture was cooled to −30° C. and a solution of the initially prepared isocyanate in 50 ml of tetrahydrofuran was then added to the mixture. Stirring was carried out for a further 16 hours at about 20° C. After the addition of ice water, the mixture was acidified with dilute hydrochloric acid. The product was extracted with ethyl acetate. The organic phase separated off was finally dried over magnesium sulfate and evaporated down. Yield: 4 g.

$^1$H-NMR (250 MHz; in CDCl$_3$): δ [ppm]=2.78 (s,3H), 6.22 (s,1H), 7.35 (d,1H).

Preliminary stage 5.1

2-Amino-4-chloro-6-fluorobenzothiazole 30 g (0.2 mol) of 2-chloro-4-fluoroaniline were reacted similarly to preliminary stage 9.1. Yield: 19.4 g.

$^1$H-NMR (400 MHz; in d$^6$-dimethyl sulfoxide): δ [ppm] =7.28 (d,1H), 7.62 (d,1H), 7.90 (s,2H).

Preliminary stage 5.2

4-Chloro-6-fluoro-2-(methylthio)benzothiazole 27 g (0.13 mol) of 2-amino-4-chloro-6-fluorobenzothiazole were reacted similarly to preliminary stage 6.1. Yield: 20 g.

$^1$H-NMR (270 MHz; in CDCl$_3$): δ [ppm]=2.80 (s,3H), 7.21 (dd,1H), 7.36 (dd,1H).

Preliminary stage 5.3

4-Chloro-6-fluoro-2-methylsulfinyl-7-nitrobenzothiazole 21.8 g (93 mmol) of 4-chloro-6-fluoro-2-(methylthio)benzothiazole were reacted similarly to preliminary stage 4.2. Yield: 21.2 g.

$^1$H-NMR (250 MHz; in CDCl$_3$): δ [ppm]=3.16 (s,3H), 7.66 (d,1H).

Preliminary stage 5.4

7-Amino-4-chloro-6-fluoro-2-(methylthio)benzothiazole 19.1 g of 4-chloro-6-fluoro-2-methylsulfinyl-7-nitrobenzothiazole were reacted similarly to preliminary stage 4.3, but refluxing was carried out for 24 hours in order to reduce both the nitro and the sulfinyl group. Yield: 12 g.

$^1$H-NMR (270 MHz; in CDCl$_3$): δ [ppm]=2.82 (s,3H), 7.20 (d,1H).

EXAMPLE 6

3-(4,6-Dichloro-2-(methylthio)benzothiazol-7-yl)-6-trifluoromethyl-2,4(1H,3H)-pyrimidinedione (compound I.20)

4.0 g (15 mmol) of 7-amino-4,6-dichloro-2-(methylthio)benzothiazole were reacted similarly to Example 5. Yield: 4.4 g.

¹H-NMR (270 MHz; in CDCl₃): δ [ppm]=2.82 (s,3H), 6.27 (s,1H), 7.66 (s,1H).

Preliminary stage 6.1

4,6-Dichloro-2-(methylthio)benzothiazole 43.7 g (0.47 mol) of dimethyl disulfide and 154.5 g (1.5 mol) of tert-butyl nitrite were added to a solution of 34 g (0.16 mol) of 2-amino-4,6-dichlorobenzothiazole in 1 liter of 1,2-dichloroethane. Stirring was carried out for 16 hours, followed by washing with water and 10% strength sodium hydroxide solution, drying over magnesium sulfate and evaporating down.

Yield: 34 g; mp.: 108° to 110° C.

Preliminary stage 6.2

4,6-Dichloro-2-methylthio-7-nitrobenzothiazole 23 g (92 mmol) of 4,6-dichloro-2-(methylthio) benzothiazole were reacted similarly to preliminary stage 4.2. However, purification of the crude product was carried out by means of silica gel chromatography (eluent: 4:1 cyclohexane/ethyl acetate). Yield: 23 g; mp.: 130° to 132° C.

Preliminary stage 6.3

7-Amino-4,6-dichloro-2-(methylthio)benzothiazole 5.5 g (19 mmol) of 4,6-dichloro-2-methylthio-7-nitrobenzothiazole were reacted similarly to preliminary stage 4.3. Yield: 5.0 g.

¹H-NMR (270 MHz; in CDCl₃): δ [ppm]=2.84 (s,3H), 4.15 (s,2H), 7.39 (s,1H).

EXAMPLE 7

3-(4-Chloro-6-fluoro-2-(methylsulfinyl) benzothiazol-7-yl)-1-methyl-6-trifluoromethyl-2,4 (1H,3H)-pyrimidinedione (compound I.22) and 3-(4-chloro-6-fluoro-2-(methylsulfonyl)-benzothiazol-7-yl)-1-methyl-6-trifluoromethyl-2,4( 1H,3H)-pyrimidinedione (compound I.23)

0.6 g (1.7 mmol) of 50% strength m-chloroperbenzoic acid was added at 0° C. to a solution of 0.7 g (1.6 mmol) of 3-(4-chloro-6-fluoro-2-(methylthio)benzothiazol-7-yl)-1-methyl-6-trifluoromethyl-2,4(1H,3H)-pyrimidinedione in 50 ml of dichloromethane. Stirring was carried out for 16 hours, followed by washing in succession with water, saturated aqueous sodium thiosulfate solution, water, 10% strength sodium hydroxide solution and water. This was followed by drying over magnesium sulfate and finally by evaporating down. The two products were separated by silica gel chromatography (eluent: 4:1 cyclohexane/methyl tert-butyl ether).

Yield: first 50 mg of compound I.23, then 0.12 g of compound I.22.

EXAMPLE 8

3-(4,6-Dichloro-2-methylbenzothiazol-7-yl)-6-trifluoromethyl-2,4(1H,3H)-pyrimidinedione (compound I.24)

3.5 g (15 mmol) of 7-amino-4,6-dichloro-2-methylbenzothiazole were reacted similarly to Example 5. Yield: 3 g.

¹H-NMR (270 MHz; in d⁶-dimethyl sulfoxide): δ [ppm]=2.86 (s,3H), 6.58 (s,1H), 8.04 (s,1H).

Preliminary stage 8.1

4,6-Dichloro-2-methyl-7-nitrobenzothiazole 6.9 g (32 mmol) of 4,6-dichloro-2-methylbenzothiazole were reacted similarly to preliminary stage 4.2. Yield: 8.3 g.

¹H-NMR (270 MHz; in CDCl₃): δ [ppm]=2.91 (s,3H), 7.73 (s,1H).

Preliminary stage 8.2

7-Amino-4,6-dichloro-2-methylbenzothiazole 8.3 g (32 mmol) of 4,6-dichloro-2-methyl-7-nitrobenzothiazole were reacted similarly to preliminary stage 4.3. Yield: 3.5 g.

¹H-NMR (270 MHz; in d⁶-dimethyl sulfoxide): δ [ppm]=2.81 (s,3H), 5.99 (s,2H), 7.47 (s,1H).

EXAMPLE 9

3-(4,6-Dichlorobenzothiazol-7-yl)-6-trifluoromethyl-2,4(1H,3H)-pyrimidinedione (compound I.26)

3 g of desired product were obtained from 3.0 g (14 mmol) of 7-amino-4,6-dichlorobenzothiazole in the manner described in Example 5.

¹H-NMR (270 MHz; in d⁶-dimethyl sulfoxide): δ [ppm]=6.56 (s,1H), 8.12 (s,1H), 9.57 (s,1H).

Preliminary stage 9.1

2-Amino-4,6-dichlorobenzothiazole 197 g (1.23 mol) of bromine were slowly added dropwise, while cooling with ice, to a solution of 200 g (1.23 mol) of 2,4-dichloroaniline and 200 g (2.46 mol) of sodium thiocyanate in 1.5 l of glacial acetic acid. Stirring was carried out for 16 hours at about 20° C., after which the solid was separated off and washed with 10% strength sodium hydroxide solution and water.

Yield: 205 g.

¹H-NMR (270 MHz; in d⁶-dimethyl sulfoxide): δ [ppm]=7.39 (d,1H), 7.80 (d,1H), 8.00 (s,2H).

Preliminary stage 9.2

2-Bromo-4,6-dichlorobenzothiazole 35 g (0.24 mol) of copper(I) bromide and 126 g (1.23 mol) of sodium bromide were added to a solution of 27 g (0.12 mol) of 2-amino-4,6-dichlorobenzothiazole in 0.5 l of acetonitrile, and 16.5 g (0.16 mol) of tert-butyl nitrite were then added dropwise. Stirring was carried out for 16 hours, after which the reaction mixture was acidified with 10% strength hydrochloric acid. The product was then extracted with methyl tert-butyl ether. The organic phase was washed with water, dried over magnesium sulfate and finally evaporated down. Purification of the crude product was carried out by means of column chromatography over silica gel (eluent: 1:1 cyclohexane/ethyl acetate). Yield: 9.1 g.

¹H-NMR (250 MHz; in d⁶-dimethyl sulfoxide): δ [ppm]=7.78 (d,1H), 8.24 (d,1H).

Preliminary stage 9.3

4,6-Dichlorobenzothiazole

A solution of 98 mmol of methyl magnesium chloride in tetrahydrofruan was added dropwise to a solution of 14 g (49 mmol) of 2-bromo-4,6-dichlorobenzothiazole in 200 ml of tetrahydrofuran, which solution had been cooled to -78° C. After 2 hours, acidification was effected with 10% strength hydrochloric acid and the product was then extracted with diethyl ether. The organic phase was washed with water, saturated aqueous sodium bicarbonate solution and water, dried over sodium sulfate and finally evaporated down. Purification of the crude product was effected by means of silica gel chromatography (eluent: 5:1 petroleum ether/methyl tert-butyl ether). Yield: 5.2 g.

$^1$H-NMR (250 MHz; in d$^6$-dimethyl sulfoxide): δ [ppm]=7.79 (d,1H), 8.36 (d,1H), 9.53 (s,1H).

Preliminary stage 9.4

4,6-Dichloro-7-nitrobenzothiazole 5.2 g (26 mmol) of 4,6-dichlorobenzothiazole were reacted similarly to preliminary stage 4.2. Yield: 5.8 g.

$^1$H-NMR (270 MHz; in d$^6$-dimethyl sulfoxide): δ [ppm]=8.17 (s,1H), 9.65 (s,1H).

Preliminary stage 9.5

7-Amino-4,6-dichlorobenzothiazole 5.8 g of 4,6-dichloro-7-nitrobenzothiazole were reacted similarly to preliminary stage 4.3. Yield: 3.0 g.

$^1$H-NMR (250 MHz; in d$^6$-dimethyl sulfoxide): δ [ppm]=6.11 (s,2H), 7.52 (d,1H), 9.38 (d,1H).

EXAMPLE 10

Ethyl 3-[4-chloro-6-fluoro-7-(6-trifluoromethyl-2,4 (1H,3H)-dioxopyrimidin-3-yl)benzothiazol-2-yl] acrylate (compound I.28)

4.0 g (13 mmol) of ethyl 3-(7-amino-4-chloro-6-fluorobenzothiazol-2-yl)acrylate were reacted similarly to Example 5.

Yield: 0.8 g.

$^1$H-NMR (270 MHz; in CDCl$_3$): δ [ppm]=1.34 (t,3H), 4.30 (q,2H), 6.31 (s,1H), 6.75 (d,1H), 7.52 (d,1H), 7.88 (d,1H), 9.30 (s,1H).

Preliminary stage 10.1

Ethyl 3-(4-chloro-6-fluorobenzothiazol-2-yl)acrylate 150 g (1.48 mol) of ethyl acrylate, 11.4 g (85 mmol) of copper (II) chloride and 11.4 g (0.11 mol) of tert-butyl nitrite were added to a solution of 12 g (59 mmol) of 2-amino-4-chloro-6-fluorobenzothiazole in 0.4 l of acetonitrile. Stirring was carried out for 3 days, after which the mixture was acidified with dilute hydrochloric acid. The product was extracted with methyl tert-butyl ether, after which the extracts were dried over magnesium sulfate and finally evaporated down. Purification of the crude product was effected by means of column chromatography over silica gel (eluent: 19:1 cyclohexane/methyl tert-butyl ether). Yield: 9,0 g.

$^1$H-NMR (400 MHz; in CDCl$_3$): δ [ppm]=1.36 (t,3H), 4.30 (q,2H), 6.74 (d,1H), 7.31 (dd,1H), 7.48 (dd,1H), 7.90 (d,1H).

Preliminary stage 10.2

Ethyl 3-(4-chloro-6-fluoro-7-nitrobenzothiazol-2-yl) acrylate 8.0 g (28 mmol) of ethyl 3-(4-chloro-6-fluorobenzothiazol-2-yl)-acrylate were reacted similarly to preliminary stage 4.2.

Yield: 9.2 g.

$^1$H-NMR (270 MHz; in d$^6$-dimethyl sulfoxide): δ [ppm]=1.31 (t,3H), 4.26 (q,2H), 7.08 (d,1H), 7.88 (d,1H), 8.22 (d,1H).

Preliminary stage 10.3

Ethyl 3-(7-amino-4-chloro-6-fluorobenzothiazol-2-yl)acrylate 10 g (30 mmol) of ethyl 3-(4-chloro-6-fluoro-7-nitrobenzo-thiazol-2-yl)acrylate were reacted similarly to preliminary stage 4.3.

Yield: 7.8 g.

$^1$H-NMR (250 MHz; in d$^6$-dimethyl sulfoxide): δ [ppm]=1.30 (t,3H), 4.25 (q,2H), 6.01 (s,2H), 6.82 (d,1H), 7.55 (d,1H), 7.82 (d,1H).

EXAMPLE 11

3-(4-Chloro-2-ethyl-6-fluorobenzothiazol-7-yl)-6-trifluoromethyl-2,4(1H,3H)-pyrimidinedione (compound I.18)

5.4 g of 7-amino-4-chloro-2-ethyl-6-fluorobenzothiazole were reacted similarly to Example 5. Yield: 5.7 g; mp.: 178° to 180° C.

Preliminary stage 11.1

4-Chloro-2-ethyl-6-fluorobenzothiazole

A solution of 0.2 mol of ethyl magnesium bromide in diethyl ether was added to a solution of 22.0 g (0.1 mol) of 2,4-dichloro-6-fluorobenzothiazole and 3.3 g (5 mmol) of dichlorobis(triphenylphosphine)nickel in 0.5 l of diethyl ether. Stirring was carried out for 2 hours, after which the mixture was poured onto saturated aqueous ammonium chloride solution. The product was extracted with diethyl ether. The combined organic phases were washed with water, dried over magnesium sulfate and finally evaporated down. Purification of the crude product was effected by means of silica gel chromatography (eluent: 8:2 cyclohexane/methyl tert-butyl ether). Yield: 10.3 g.

$^1$H-NMR (270 MHZ; in CDCl$_3$): δ [ppm]=1.46 (t,3H), 3.16 (q,2H), 7.25 (dd,1H), 7.43 (dd,1H).

Preliminary stage 11.2

4-Chloro-2-ethyl-6-fluoro-7-nitrobenzothiazole 9 g (42 mmol) of 4-chloro-2-ethyl-6-fluorobenzothiazole were reacted similarly to preliminary stage 4.2. Yield: 8.4 g; mp.: 70° to 73° C.

Preliminary stage 11.3

7-Amino-4-chloro-2-ethyl-6-fluorobenzothiazole 8.5 g (33 mmol) of 4-chloro-2-ethyl-6-fluoro-7-nitrobenzothiazole were reacted similarly to preliminary stage 4.3. Yield: 6.4 g.

$^1$H-NMR (270 MHz; in CDCl$_3$): δ [ppm]=7.2 (t,3H), 3.16 (q,2H), 7.21 (d,1H), 8.00 (s,2H).

Table 5 shows, in addition to the above active ingredients, further substituted benzothiazoles of the formula I, which were prepared in the same manner or can be prepared in a similar manner:

TABLE 5

(R² = CF₃, R³ = H, R⁵ = Cl, X¹, X² = O)

| No. | R¹ | R⁴ | Y | R⁶ | ¹H-NMR[δ in ppm]/MS[m]/Mp. |
|---|---|---|---|---|---|
| I.1 | H | H | — | Cl | 6.25(s, 1H), 7.00(d, 1H), 7.37(d, 1H) |
| I.2 (=Ia.1) | CH₃ | H | — | Cl | 3.48(s, 3H), 6.40(s, 1H), 7.27(d, 1H), 7.65(d, 1H) |
| I.3 (=Ic.19) | CH₃ | H | O | C₂H₅ | 1.48(t, 3H), 3.56(s, 3H), 4.70(q, 2H), 6.40(s.1H), 7.04(d, 1H), 7.48(d, 1H) |
| I.4 | H | F | — | Cl | 6.43(s, 1H), 8.06(d, 1H) |
| I.5 (=Ia.2) | CH₃ | F | — | Cl | 3.62(s, 3H), 6.40(s, 1H), 7.46(d, 1H) |
| I.6 | H | F | O | C₂H₅ | 1.49(t, 3H), 4.65(q, 2H), 6.50(s, 1H), 7.82(d, 1H) |
| I.7 (=Ic.20) | CH₃ | F | O | C₂H₅ | 1.47(t, 3H), 3.56(s, 3H), 4.67(q, 2H), 6.38(s, 1H), 7.33(d, 1H) |
| I.8 | H | F | O | n-C₃H₇ | 0.95(t, 3H), 1.72(sex, 2H), 4.53(t, 2H), 6.46(s, 1H)7.82(d, 1H) |
| I.9 (=Ic.23) | CH₃ | F | O | n-C₃H₇ | 1.04(t, 3H), 1.88(sex, 2H), 3.58(s, 3H), 4.58(t, 2H), 6.39(s, 1H), 7.32(d, 1H) |
| I.10 | H | F | S | CH₃ | 2.78(s, 3H), 6.22(s, 1H), 7.35(d, 1H) |
| I.11 (=Ie.17) | CH₃ | F | S | CH₃ | 2.78(s, 3H), 3.56(s, 3H), 6.38(s, 1H), 7.38(d, 1H) |
| I.12 | H | H | O | C₂H₅ | 1.50(t, 3H), 4.69(q, 2H), 6.26(s, 1H), 7.05(d, 1H), 7.50(d, 1H) |
| I.13 | H | F | S | C₂H₅ | 1.50(t, 3H), 3.32(q, 2H), 6.33(s, 1H), 7.15(d, 1H) |
| I.14 (=Ie.20) | CH₃ | F | S | C₂H₅ | 1.51(t, 3H), 3.37(q, 2H), 3.59(s, 3H), 6.40(s, 1H), 7.40(d, 1H) |
| I.15 | C₂H₅ | F | — | Cl | 1.39(t, 3H), 4.06(q, 2H), 6.38(s, 1H), 7.49(d, 1H) |
| I.16 | H | F | — | CH₃ | 2.85(s, 3H), 6.26(s, 1H), 7.45(d, 1H) |
| I.17 (=Ia.17) | CH₃ | F | — | CH₃ | 2.85(s, 3H), 3.59(s, 3H), 6.41(s, 1H), 7.45(d, 1H) |
| I.18 | H | F | — | C₂H₅ | 1.36(t, 3H), 3.17(q, 2H), 6.55(s, 1H), 7.92(d, 1H) |
| I.19 (=Ia.20) | CH₃ | F | — | C₂H₅ | 1.45(t, 3H), 3.15(q, 2H), 3.60(s, 3H), 6.41(s, 1H), 7.46(d, 1H) |
| I.20 | H | Cl | S | CH₃ | 2.82(s, 3H), 6.27(s, 1H), 7.66(s, 1H) |
| I.21 (=Ie.18) | CH₃ | Cl | S | CH₃ | 2.81(s, 3H), 3.60(s, 3H), 6.40(s, 1H), 7.65(s, 1H) |
| I.22 (=Ig.17) | CH₃ | F | SO | CH₃ | 441[M]⁺, 426[M-CH₃]⁺ |
| I.23 (=Ii.17) | CH₃ | F | SO₂ | CH₃ | 3.43(s, 3H), 3.60(s, 3H), 6.42(s, 1H), 7.64(d, 1H) |
| I.24 | H | Cl | — | CH₃ | 2.86(s, 3H), 6.58(s, 1H), 8.04 (s, 1H) |
| I.25 (=Ia.18) | CH₃ | Cl | — | CH₃ | 2.86(s, 3H), 3.45(s, 3H), 6.71(s, 3H), 8.06(s, 3H) |
| I.26 | H | Cl | — | H | 6.56(s, 1H), 8.12(s, 1H), 9.57(s, 1H) |
| I.27 (=Ia.15) | CH₃ | Cl | — | H | |
| I.28 | H | F | — | CH=CH—CO₂C₂H₅ | 1.34(t, 3H), 4.30(q, 2H), 6.31(s, 1H), 6.75(d, 1H), 7.52(d, 1H), 7.88(d, 1H), 9.30(s, 1H) |
| I.29 (=Ia.182) | CH₃ | F | — | CH=CH—CO₂C₂H₅ | 1.34(t, 3H), 3.60(s, 3H), 4.30(q, 2H), 6.42(s, 1H), 6.74(d, 1H), 7.51(d, 1H), 7.87(d, 1H) |
| I.30 | H | F | S | n-C₃H₇ | 1.01(t, 3H), 1.80(sext, 2H), 3.35(t, 2H), 6.43(s, 1H), 7.90(d, 1H) |
| I.31 (=Ie.23) | CH₃ | F | S | n-C₃H₇ | 1.08(t, 3H), 1.87(sext, 2H), 3.33(t, 2H), 3.58(s, 3H), 6.39(s, 1H), 7.38(d, 1H) |
| I.32 | H | Cl | S | C₂H₅ | 1.45(t, 3H), 3.39(q, 2H), 6.52(s, 1H), 8.02(s, 1H) |
| I.33 (=Ie.21) | CH₃ | Cl | S | C₂H₅ | 150–153° C. |
| I.34 | H | Cl | S | n-C₃H₇ | 1.01(t, 3H), 1.80(sext, 2H), 3.36(t, 2H), 6.54(s, 1H), 8.02(s, 1H) |

TABLE 5-continued

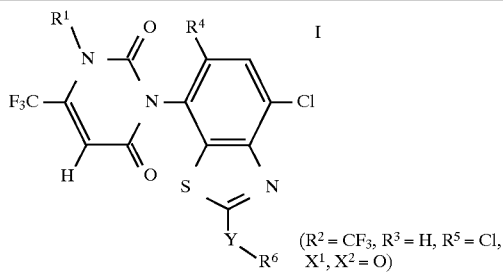

($R^2$ = CF$_3$, $R^3$ = H, $R^5$ = Cl, $X^1$, $X^2$ = O)

| No. | $R^1$ | $R^4$ | Y | $R^6$ | $^1$H-NMR[δ in ppm]/MS[m]/Mp. |
|---|---|---|---|---|---|
| I.35 (=Ie.24) | CH$_3$ | Cl | S | n-C$_3$H$_7$ | 1.08(t, 3H), 1.87(sext, 2H), 3.32(t, 2H), 3.58(s, 3H), 6.38(s, 1H), 7.61(s, 1H) |
| I.36 | H | Cl | S | CH(CH$_3$)$_2$ | 1.49(d, 6H), 4.07(m, 1H), 6.52(s, 1H), 8.03(s, 1H) |
| I.37 (=Ie.27) | CH$_3$ | Cl | S | CH(CH$_3$)$_2$ | 1.52(d, 6H), 3.59(s, 3H), 4.14(m, 1H), 6.39(s, 1H), 7.62(s, 1H) |
| I.38 | H | F | — | CH(CH$_3$)$_2$ | |
| I.39 (=Ia.26) | CH$_3$ | F | — | CH(CH$_3$)$_2$ | |
| I.40 | H | Cl | — | Cl | |
| I.41 | CH$_3$ | Cl | — | Cl | 429[M]$^+$, 394[M-Cl]$^+$ |

EXAMPLE 12

7-Amino-4-chloro-6-fluoro-2-(methylsulfinyl)benzothiazole (compound XIV.1; =XIVa.2)

23.0 g of 4-chloro-6-fluoro-2-methylsulfinyl-7-nitrobenzothiazole were added in small portions to a mixture of 455 ml of water, 32.6 ml of concentrated hydrochloric acid and 37.2 g of iron powder at the reflux temperature. After the end of the addition, refluxing was continued for a further 2 hours. The mixture was cooled and 200 ml of ethyl acetate were then added, after which the inorganic salts were filtered off. The organic phase was washed with water, dried over sodium sulfate and finally evaporated down. The crude product obtained could be further processed without further purification.

$^1$H-NMR (250 MHz; in d$^6$-dimethyl sulfoxide): see Table 6.

Table 6 shows, in addition to the abovementioned aniline derivatives XIV, also further aniline derivatives XIV which were prepared in the same manner or can be prepared in a similar manner:

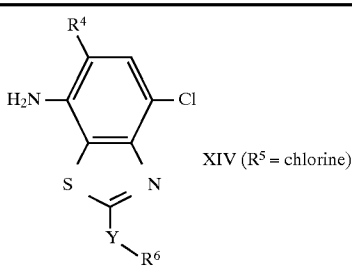

XIV ($R^5$ = chlorine)

| No. | $R^4$ | Y | $R^6$ | $^1$H-NMR[δ in ppm] |
|---|---|---|---|---|
| XIV.1 (=XIVa.2) | F | SO | CH$_3$ | 3.20(s, 3H), 6.15(s, 2H), 7.60 d, 1H) |
| XIV.2 (=XIVb.3) | Cl | SO$_2$ | CH$_3$ | 3.61(s, 3H), 6.50(s, 2H), 7.77(s, 1H) |

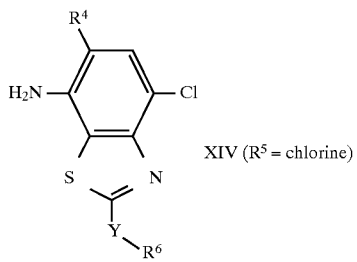

XIV ($R^5$ = chlorine)

| No. | $R^4$ | Y | $R^6$ | $^1$H-NMR[δ in ppm] |
|---|---|---|---|---|
| XIV.3 (=XIVa.6) | F | SO | C$_2$H$_5$ | 1.21(t, 3H), 3.18(m, 1H), 3.40(m, 1H), 6.14(s, 2H), 7.60(d, 1H) |

EXAMPLE 13

4,6-Dichloro-7-isocyanato-2-(methylsulfonyl)benzothiazole (compound XI.1; =XIb.3)

5 g (17 mmol) of 7-amino-4,6-dichloro-2-(methylsulfonyl)benzothiazole and 17 g (85 mmol) of diphosgene in 200 ml of toluene were refluxed for 8 hours, after which the reaction mixture was evaporated down.

The crude product obtained was reacted further without purification.

IR (film): ν=2272 cm$^{-1}$.

EXAMPLE 14

4-Chloro-2-ethylsulfinyl-6-fluoro-7-isocyanatobenzothiazole (compound XI.2; =XIa.6) was prepared similarly to Example 7.

IR (film): ν=2264 cm$^{-1}$.

Use Examples (herbicidal activity)

The herbicidal action of the substituted benzothiazoles I were demonstrated by the following greenhouse experiments:

The culture vessels used were plastic flowerpots containing loamy sand with about 3.0% of humus as a substrate. The seeds of the test plants were sown separately according to species.

In the preemergence treatment, the active ingredients suspended or emulsified in water were applied directly after sowing, by means of finely distributing nozzles. The vessels were lightly sprinkle-irrigated in order to promote germination and growth and were then covered with transparent plastic covers until the plants had begun to grow. This covering ensures uniform germination of the test plants, provided that this has not been adversely affected by the active ingredients. The application rate for the preemergence treatment was 0.0156 or 0.0078 kg/ha a.i. (active ingredient).

For the postemergence treatment, the test plants were first grown to a height of growth of from 3 to 15 cm, depending on the form of growth, before being treated with the active ingredients suspended or emulsified in water. For this purpose, the test plants were either directly sown and grown in the same vessels or grown separately as seedlings and then transplanted into the test vessels a few days before the treatment. The application rate for the postemergence treatment was 0.0156, 0.0078 or 0.0039 kg/ha a.i. (active ingredient).

The plants were kept at from 10° to 25° C. or from 20° to 35° C., according to species. The test period extended over from 2 to 4 weeks. During this time, the plants were tended and their reaction to the individual treatments was evaluated.

Evaluation was based on a scale from 0 to 100. 100 means no emergence of the plants or complete destruction of at least the above-ground parts and 0 means no damage or normal course of growth.

The plants used in the greenhouse experiments consisted of the following species:

| Botanical Name | Common Name |
| --- | --- |
| Amaranthus retroflexus | redroot pigweed |
| Galium aparine | catchweed bedstraw |
| Ipomoea subspecies | morning glory |
| Setaria faberii | giant foxtail |
| Sinapis alba | white mustard |
| Solanum nigrum | black nightshade |
| Zea mays | Indian corn |

At an application rate of 0.0156 or 0.0078 kg/ha a.i., compound No. I.7 showed a very good herbicidal action against Setaria faberii in corn in the preemergence method. In contrast, the comparative compound A

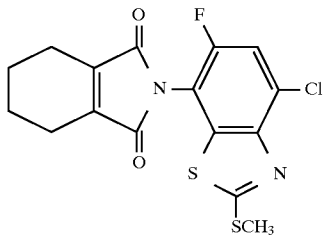

(A)

disclosed in DE-A 42 41 658 (No. 1.01) had no effect with regard to Setaria faberii.

Compound No. I.7 was also very effective against Amaranthus retroflexus, Galium aparine, Ipomoea subspecies and Solanum nigrum in the postemergence method at an application rate of 0.0156 or 0.0078 kg/ha a.i.

At an application rate of 0.0078 or 0.0039 kg/ha a.i. in the postemergence method, compound No. I.5 had a better herbicidal action against Amaranthus retroflexus, Galium aparine, Ipomoea subspecies and Sinapis alba than the comparative compound B

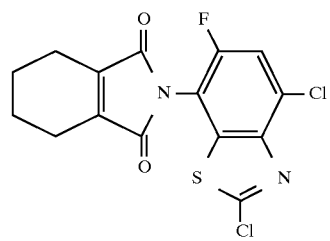

(B)

disclosed in WO 92/20675 (No. 1.01).

Use Examples (desiccant/defoliant activity)

The test plants used were young, 4-leaf cotton plants (without cotyledons), which were grown under greenhouse conditions (relative humidity from 50 to 70%; day/night temperature 27°/20° C.).

The foliage of the young cotton plants was sprayed to run off with aqueous formulations of the active ingredients (with the addition of 0.15% by weight, based on the spray liquor, of the fatty alcohol alkoxylate Plurafac® LF 700[1]). The amount of water applied was equivalent to 1000 l/ha. After 13 days, the number of dropped leaves and the degree of defoliation in % were determined. ≠[1] -¹ a low-foam, nonionic surfactant from BASF AG No defoliation occurred in the case of the untreated control plants.

We claim:

1. A substituted benzothiazole of the formula I

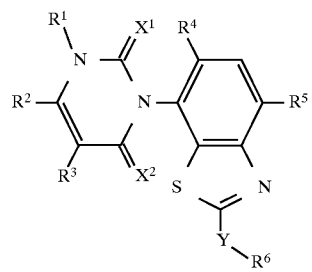

where $X^1$ and $X^2$, independently of one another, are each oxygen or sulfur;

$R^1$ is hydrogen, amino, $C_1$–$C_6$-alkyl or $C_1$–$C_6$-haloalkyl, $R^2$ is hydrogen, halogen, $C_1$–$C_6$-alkyl, $C_1$–$C_6$-haloalkyl, $C_1$–$C_6$-alkylthio, $C_1$–$C_6$-alkylsulfinyl or $C_1$–$C_6$-alkylsulfonyl;

$R^3$ is hydrogen, halogen or $C_1$–$C_6$-alkyl;

$R^4$ is hydrogen or halogen;

$R^5$ is cyano, halogen, $C_1$–$C_6$-alkyl, $C_1$–$C_6$-haloalkyl, $C_1$–$C_6$-alkoxy or $C_1$–$C_6$-haloalkoxy;

Y is a chemical bond, oxygen, sulfur, —SO— or —SO$_2$—;

$R^6$ is hydrogen, cyano, halogen, $C_3$–$C_6$-cycloalkyl, $C_1$–$C_6$-haloalkyl, $C_3$–$C_6$-alkenyl, $C_3$–$C_6$-haloalkenyl, $C_3$–$C_6$-alkynyl or $C_1$–$C_6$-alkyl, it being possible for the stated cycloalkyl, alkyl, alkenyl and alkynyl radicals to be substituted by cyano, $C_1$–$C_6$-alkoxy, $C_1$–$C_6$-alkylthio, ($C_1$–$C_6$-alkoxy)carbonyl, $C_1$–$C_6$-alkylaminocarbonyl, di($C_1$–$C_6$-alkyl)aminocarbonyl, ($C_1$–$C_6$-alkyl)carbonyloxy, halo-$C_1$–$C_6$-alkoxy, halo-$C_1$–$C_6$-alkylthio or $C_3$–$C_6$-cycloalkyl, with the proviso that $R^6$ may be cyano only when Y is a chemical bond, oxygen or sulfur and $R^6$ may be halogen only when Y is a chemical bond, and the agriculturally useful salts of I.

2. A herbicide containing a herbicidal amount of at least one substituted benzothiazole of the formula I or of an agriculturally useful salt of I, as claimed in claim 1, and at least one inert liquid or solid carrier and, optionally, at least one surfactant.

3. A plant desiccant or defoliant containing an amount, effective for desiccation or defoliation, of at least one substituted benzothiazole of the formula I or of an agriculturally useful salt of I, as claimed in claim 1, and at least one inert liquid or solid carrier and, optionally, at least one surfactant.

4. A process for the preparation of a herbicide, wherein a herbicidal amount of at least one substituted benzothiazole of the formula I or of an agriculturally useful salt of I, as claimed in claim 1, and at least one inert liquid or solid carrier and, optionally, at least one surfactant are mixed.

5. A process for the preparation of a desiccant or defoliant, wherein an amount, effective for desiccation or defoliation, of at least one substituted benzothiazole of the formula I or of an agriculturally useful salt of I, as claimed in claim 1, and at least one inert liquid or solid carrier and, optionally, at least one surfactant are mixed.

6. A method for controlling undesirable plant growth, wherein a herbicidal amount of at least one substituted benzothiazole of the formula I or of an agriculturally useful salt of I, as claimed in claim 1, is allowed to act on plants, on their habitat or on seed.

7. A method for desiccating or defoliating plants, wherein an amount, effective for desiccation or defoliation, of at least one substituted benzothiazole of the formula I or of an agriculturally useful salt of I, as claimed in claim 1, is allowed to act on plants.

8. A process for the preparation of a substituted benzothiazole of the formula I as claimed in claim 1, wherein either a) a substituted benzothiazole of the formula I where $R^1$ is hydrogen and $X^1$ is oxygen

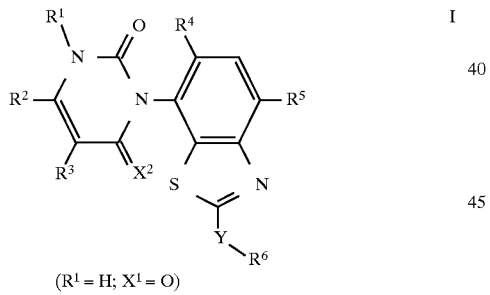

($R^1$ = H; $X^1$ = O)

is alkylated or aminated, or b) a substituted benzothiazole of the formula I where $X^2$ is oxygen

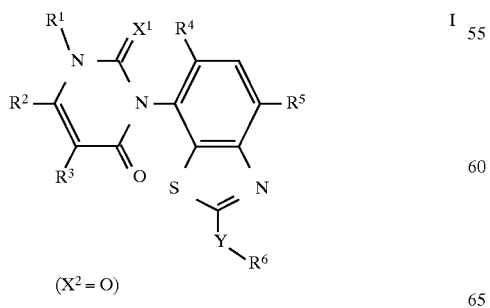

($X^2$ = O)

is treated with a sulfurizing reagent, or c) a substituted benzothiazole of the formula I, in which $YR^6$ is chlorine, bromine, —$SO_2$-alkyl or —$SO_2$-haloalkyl, is reacted with an alcohol $HOR^6$ or mercaptan $HSR^6$, or d) a substituted benzothiazole of the formula I where $X^1$ and $X^2$ are each oxygen and Y is sulfur or —SO—

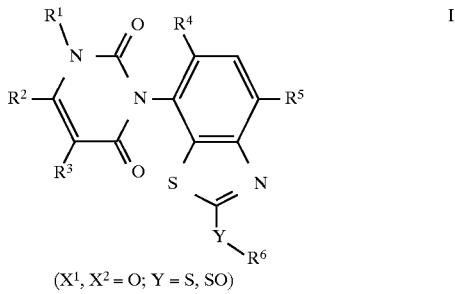

($X^1, X^2$ = O; Y = S, SO)

is oxidized, or d) an enaminoester of the formula IV

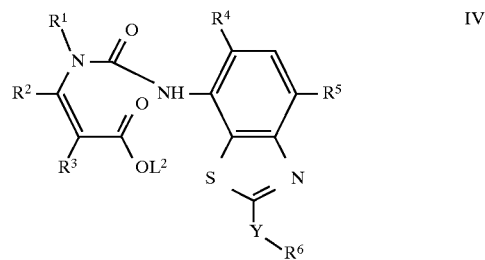

or an enaminocarboxylate of the formula V

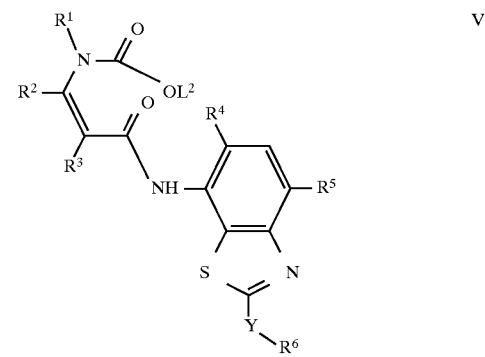

is cyclized, or f) a 2-aminobenzothiazole of the formula VI

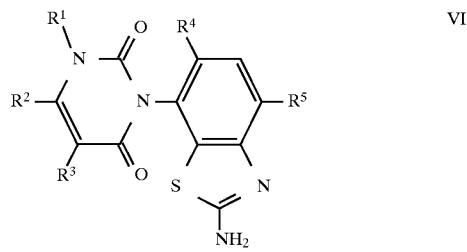

is diazotized and the product is subjected to a Sandmeyer reaction or a variant thereof.

* * * * *